(12) United States Patent
Atwal et al.

(10) Patent No.: US 7,943,329 B2
(45) Date of Patent: May 17, 2011

(54) MODULATORS OF NEURONAL REGENERATION

(75) Inventors: Jasvinder Atwal, San Carlos, CA (US); Marc Tessier-Lavigne, Woodside, CA (US)

(73) Assignee: Genentech, Inc., South San Francisco, CA (US)

(*) Notice: Subject to any disclaimer, the term of this patent is extended or adjusted under 35 U.S.C. 154(b) by 363 days.

(21) Appl. No.: 11/983,775

(22) Filed: Nov. 9, 2007

(65) Prior Publication Data

US 2009/0169542 A1    Jul. 2, 2009

Related U.S. Application Data

(60) Provisional application No. 60/865,772, filed on Nov. 14, 2006, provisional application No. 60/890,416, filed on Feb. 16, 2007.

(51) Int. Cl.
*G01N 33/567* (2006.01)
(52) U.S. Cl. ........................ 435/7.21; 435/7.1
(58) Field of Classification Search ............. None
See application file for complete search history.

(56) References Cited

U.S. PATENT DOCUMENTS

| | | | | |
|---|---|---|---|---|
| 2003/0049254 A1* | 3/2003 | Kaufman et al. | ......... | 424/144.1 |
| 2003/0113326 A1* | 6/2003 | He et al. | ..................... | 424/146.1 |
| 2003/0170690 A1 | 9/2003 | Shatz | | |
| 2005/0048520 A1 | 3/2005 | Strittmatter | | |

FOREIGN PATENT DOCUMENTS

WO    WO 03/51834 A2    6/2003

OTHER PUBLICATIONS

Atwal JK et al. PirB is a functional receptor for myelin inhibitors of axonal regeneration. Science, Nov. 2008; 322:967-970.*
Filbin MT. PirB, a second receptor for the myelin inhibitors of axonal regeneration Nogo66, MAG, and OMgp: Implications for regeneration in vivo. Neuron, Dec. 2008; 60:740-742.*
Giger RJ et al. Mechanisms of CNS myelin inhibition: evidence for distinct and neuronal cell type specific receptor systems. Restor Neurol Neurosci. 2008; 26(2-3):97-115.*
Thams S et al. Classical major histocompatibility complex I molecules in motoneurons: new actors at the neuromuscular junction. J Neurosci. Oct. 2009; 29(43):13503-13515.*
Pushparaj PN and Melendez AJ. Short interfering RNA (siRNA) as a novel therapeutic. Clin Exp Pharmacol Physiol. 2006; 33:504-510.*
Shiroishi, et al., "Human inhibitory receptors Ig-like transcript 2 (ILT2) and ILT4 compete with CD8 for MHC class 1 binding and bind preferentially to HLA-G", PNAS vol. 100, No. 15, pp. 8856-8861, (2003).
Borges, et al., "A family of human lymphoid and myeloid Ig-like receptors, some of which bind to MHC class 1 molecules", The Journal of Immunology, 159: 5192-5196, (1997).
Boulanger, et al., "Immune signaling in neural development, synaptic plasticity and disease", Nature Reviews, vol. 5, pp. 521-531, (2004).

Chen, et al., "Nogo-A is a myelin-associated neurite outgrowth inhibitor and an antigen for monoclonal antibody IN-1", Nature, vol. 403, pp. 434-439, (2000).
Colonna, et al., "A common inhibitory receptor for major histocompatibility complex class 1 molecules on human lymphoid and myelomonocytic cells", J. Exp. Med., vol. 186, No. 11, pp. 1809-1818, (1997).
Fournier, et al., "Identification of a receptor mediating Nogo-66 inhibition of axonal regeneration", Nature, vol. 409, pp. 341-346, (2001).
GrandPre, et al., "Identification of the Nogo inhibitor of axon regeneration as a reticulon protein", Nature, vol. 403, pp. 439-444, (2000).
GrandPre, et al., "Nogo-66 receptor antagonist peptide promotes axonal regeneration", Nature, vol. 417, pp. 547-551, (2002).
Hayami, et al., "Molecular cloning of a novel murine cell-surface glycoprotein homologous to killer cell inhibitory receptors", The Journal of biological chemistry, vol. 272, No. 11, pp. 7320-7327, (1996).
Kim, et al., "Nogo-66 receptor prevents raphespinal and rubrospinal axon regeneration and limits functional recovery from spinal cord injury", Neuron, vol. 44, pp. 439-451, (2004).
Kottis, et al., "Oligodendrocyte-myelin glycoprotein (OMgp) is an inhibitor of neurite outgrowth", Journal of Neurochemistry, 82: 1566-1569, (2002).
Kubagawa, et al., "A novel pair of immunglobulin-like receptors expressed by B cells and myeloid cells", PNAS, vol. 94, pp. 5261-5266, (1997).
Li, et al., "Delayed systemic nogo-66 receptor antagonist promotes recovery from spinal cord injury", The Journal of Neuroscience, 23(10): 4219-4227, (2003).
Liang, et al., "HLA-G inhibits the functions of murine dendritic cells via the PIR-B immune inhibitory receptor", Eur. J. Immunol., 32: 2418-2426, (2002).
McKerracher, et al., "Identification of myelin-associated glycoprotein as a major myelin-derived inhibitor of neurite growth", Neuron, vol. 13, pp. 805-811, (1994).
Nakamura, et al., "Exacerbated graft-versus-host disease in Pirb$^{-/-}$ mice", Nature Immunology, vol. 5, No. 6, pp. 623-629, (2004).
Prinijha, et al., "Inhibitor of neurite outgrowth in humans", Nature, vol. 403, pp. 383-384, (2000).
Samaridis, et al., "Cloning of novel immunoglobulin superfamily receptors expressed on human myeloid and lymphoid cells: structural evidence for new stimulatory and inhibitory pathways", Eur. J. Immunol., 27: 660-665, (1997).
Syken, et al., "PirB restricts ocular-dominance plasticity in visual cortex", Science, vol. 313, pp. 1795-1800, (2006).
Takai, et al., "Activating and inhibitory nature of the murine paired immunoglobulin-like receptor family", Immunological Reviews, vol. 181, pp. 215-222, (2001).
Takai, et al., Paired immunoglobulin-like receptors and their MHC class recognition, Immunology, 115, pp. 433-440, (2005).
Wang, et al., "Oligodendrocyte-myelin glycoprotein is a nogo receptor ligand that inhibits neurite outgrowth", Nature, vol. 417, pp. 941-944, (2002).
Wang, et al., "p75 interacts with the Nogo receptor as a co-receptor for Nogo, MAG and OMgp", Nature, vol. 420, pp. 74-78, (2002).
Wong, et al., "A $p75^{NTR}$ and Nogo receptor complex mediates repulsive signaling by myelin-associated glycoprotein", Nature Neuroscience, vol. 5, No. 12, pp. 1302-1308, (2002).
Zheng, et al., "Genetic deletion of the Nogo receptor does not reduce neurite inhibition in vitro or promote corticospinal tract regeneration in vivo", PNAS, vol. 102, No. 4, pp. 1205-1210, (2005).

* cited by examiner

*Primary Examiner* — Elizabeth C. Kemmerer
*Assistant Examiner* — Kimberly A. Ballard
(74) *Attorney, Agent, or Firm* — Irene Pleasure; Ginger R. Dreger; Arnold & Porter LLP

(57) ABSTRACT

The present invention provides methods and compositions related to CNS function and diseases.

25 Claims, 15 Drawing Sheets

FIG. 5

PirB (mouse) sequence (SEQ ID NO: 1)

```
  1 msctftallr lgltlslwip vltgslpkpi lrvqpdsvvs rwtkvtffce etiganeyrl
 61 ykdgklyktv tknkqkpank aefslsnvdl rnaggyrcsy stqykssgys dplelvvtgd
121 ywtpsllaqa spvvtsggyv tlqceswhnd hkfiltvegp qklswtqdsq ynystrkyha
181 lfsvgpvtpn qrwicrcysy drnrpyvwsp psesvellvs gnlqkptika epgpviaskr
241 amtiwcqgnl daevyflhne gsqktqstqt lqqpgnkgkf fipsmtrqha gqyrcycygs
301 agwsqpsdtl elvvtgiyeh ykprlsvlps pvvtaggnmt lhcasdfhyd kfiltkedkk
361 fgnsldtehi sssrqyralf iigpttptht gtfrcygyfk napqlwsvps dlqqilisgl
421 skkpsllthq ghildpgmtl tlqcysdiny drfalhkvgg adimqhssqq tdtgfsvanf
481 tlgyvssstg gqyrcygahn lssewsasse pldilitgql pltpslsvkp nhtvhsgetv
541 sllcwsmdsv dtfilskegs aqqplrlksk shdqqsqaef smsavtshls gtyrcygaqn
601 ssfyllssas apveltvsgp ietstppptm smplgglhmy lkaligvsva filflfilif
661 illrrrhrgk frkdvqkekd lqlssgaeep itrkgelqkr pnpaaatqee slyasvedmq
721 tedgvelnsw tppeedpqge tyaqvkpsrl rkaghvspsv msreqlntey eqaeegqgan
781 nqaaesgesq dvtyaqlcsr tlrqgaaasp lsqageapee psvyatlaaa rpeavpkdve
841 q
```

LILRB2 (human) sequence (SEQ ID NO:2)

```
  1 mtpivtvlic lglslgprth vqtgtipkpt lwaepdsvit qgspvtlscq gsleaqeyrl
 61 yrekksaswi trirpelvkn gqfhipsitw ehtgrygcqy ysrarwsels dplvlvmtga
121 ypkptlsaqp spvvtsggrv tlqcesqvaf ggfilckege dehpqclnsq phargssrai
181 fsvgpvspnr rwshrcygyd lnspyvwssp sdllellvpg vskkpslsvq pqpvvapges
241 ltlqcvsdvg ydrfvlykeg erdlrqlpgr qpqaglsqan ftlgpvsrsy ggqyrcygay
301 nlssewsaps dpldilitgq ihgtpfisvq pgptvasgen vtllcqswrq fhtflltkag
361 aadaplrlrs iheypkyqae fpmspvtsah agtyrcygsl nsdpyllshp seplelvvsg
421 psmgsspppt gpistpaqpe dqpltptgsd pqsglqrhlg vvigilvavv llllllllf
481 lilrhrrqgk hwtstqrkad fqhpagavgp eptdrglqwr sspaadaqee nlyaavkdtq
541 pedgvemdtr aaaseapqdv tyaqlhsltl rrkateppps qereppaeps iyatlaih
```

LILRB1, transcript variant 1:

MTPILTVLICLGLSLGPRTHVQAGHLPKPTLWAEPGSVITQGSPVTLRCQGGQET
QEYRLYREKKTALWITRIPQELVKKGQFPIPSITWEHAGRYRCYYGSDTAGRSES
SDPLELVVTGAYIKPTLSAQPSPVVNSGGNVILQCDSQVAFDGFSLCKEGEDEHP
QCLNSQPHARGSSRAIFSVGPVSPSRRWWYRCYAYDSNSPYEWSLPSDLLELLVL
GVSKKPSLSVQPGPIVAPEETLTLQCGSDAGYNRFVLYKDGERDFLQLAGAQPQ
AGLSQANFTLGPVSRSYGGQYRCYGAHNLSSEWSAPSDPLDILIAGQFYDRVSLS
VQPGPTVASGENVTLLCQSQGWMQTFLLTKEGAADDPWRLRSTYQSQKYQAEF
PMGPVTSAHAGTYRCYGSQSSKPYLLTHPSDPLELVVSGPSGGPSSPTTGPTSTSG
PEDQPLTPTGSDPQSGLGRHLGVVIGILVAVILLLLLLLLFLILRHRRQGKHWTS
TQRKADFQHPAGAVGPEPTDRGLQWRSSPAADAQEENLYAAVKHTQPEDGVE
MDTRSPHDEDPQAVTYAEVKHSRPRREMASPPSPLSGEFLDTKDRQAEEDRQMD
TEAAASEAPQDVTYAQLHSLTLRREATEPPPSQEGPSPAVPSIYATLAIH

FIGURE 9

LILRB1, transcript variant 2:

MTPILTVLICLGLSLGPRTHVQAGHLPKPTLWAEPGSVITQGSPVTLRCQGGQET
QEYRLYREKKTALWITRIPQELVKKGQFPIPSITWEHAGRYRCYYGSDTAGRSES
SDPLELVVTGAYIKPTLSAQPSPVVNSGGNVILQCDSQVAFDGFSLCKEGEDEHP
QCLNSQPHARGSSRAIFSVGPVSPSRRWWYRCYAYDSNSPYEWSLPSDLLELLVL
GVSKKPSLSVQPGPIVAPEETLTLQCGSDAGYNRFVLYKDGERDFLQLAGAQPQ
AGLSQANFTLGPVSRSYGGQYRCYGAHNLSSEWSAPSDPLDILIAGQFYDRVSLS
VQPGPTVASGENVTLLCQSQGWMQTFLLTKEGAADDPWRLRSTYQSQKYQAEF
PMGPVTSAHAGTYRCYGSQSSKPYLLTHPSDPLELVVSGPSGGPSSPTTGPTSTSA
GPEDQPLTPTGSDPQSGLGRHLGVVIGILVAVILLLLLLLLFLILRHRRQGKHWT
STQRKADFQHPAGAVGPEPTDRGLQWRSSPAADAQEENLYAAVKHTQPEDGVE
MDTRQSPHDEDPQAVTYAEVKHSRPRREMASPPSPLSGEFLDTKDRQAEEDRQM
DTEAAASEAPQDVTYAQLHSLTLRREATEPPPSQEGPSPAVPSIYATLAIH

FIGURE 10

LILRB1, transcript variant 3:

MTPILTVLICLGLSLGPRTHVQAGHLPKPTLWAEPGSVITQGSPVTLRCQGGQET
QEYRLYREKKTALWITRIPQELVKKGQFPIPSITWEHAGRYRCYYGSDTAGRSES
SDPLELVVTGAYIKPTLSAQPSPVVNSGGNVILQCDSQVAFDGFSLCKEGEDEHP
QCLNSQPHARGSSRAIFSVGPVSPSRRWWYRCYAYDSNSPYEWSLPSDLLELLVL
GVSKKPSLSVQPGPIVAPEETLTLQCGSDAGYNRFVLYKDGERDFLQLAGAQPQ
AGLSQANFTLGPVSRSYGGQYRCYGAHNLSSEWSAPSDPLDILIAGQFYDRVSLS
VQPGPTVASGENVTLLCQSQGWMQTFLLTKEGAADDPWRLRSTYQSQKYQAEF
PMGPVTSAHAGTYRCYGSQSSKPYLLTHPSDPLELVVSGPSGGPSSPTTGPTSTSA
GPEDQPLTPTGSDPQSGLGRHLGVVIGILVAVILLLLLLLLFLILRHRRQGKHWT
STQRKADFQHPAGAVGPEPTDRGLQWRSSPAADAQEENLYAAVKHTQPEDGVE
MDTRSPHDEDPQAVTYAEVKHSRPRREMASPPSPLSGEFLDTKDRQAEEDRQMD
TEAAASEAPQDVTYAQLHSLTLRREATEPPPSQEGPSPAVPSIYATLAIH

FIGURE 11

LILRB1, transcript variant 4:

MTPILTVLICLGLSLGPRTHVQAGHLPKPTLWAEPGSVITQGSPVTLRCQGGQET
QEYRLYREKKTALWITRIPQELVKKGQFPIPSITWEHAGRYRCYYGSDTAGRSES
SDPLELVVTGAYIKPTLSAQPSPVVNSGGNVILQCDSQVAFDGFSLCKEGEDEHP
QCLNSQPHARGSSRAIFSVGPVSPSRRWWYRCYAYDSNSPYEWSLPSDLLELLVL
GVSKKPSLSVQPGPIVAPEETLTLQCGSDAGYNRFVLYKDGERDFLQLAGAQPQ
AGLSQANFTLGPVSRSYGGQYRCYGAHNLSSEWSAPSDPLDILIAGQFYDRVSLS
VQPGPTVASGENVTLLCQSQGWMQTFLLTKEGAADDPWRLRSTYQSQKYQAEF
PMGPVTSAHAGTYRCYGSQSSKPYLLTHPSDPLELVVSGPSGGPSSPTTGPTSTSG
PEDQPLTPTGSDPQSGLGRHLGVVIGILVAVILLLLLLLLFLILRHRRQGKHWTS
TQRKADFQHPAGAVGPEPTDRGLQWRSSPAADAQEENLYAAVKHTQPEDGVE
MDTRQSPHDEDPQAVTYAEVKHSRPRREMASPPSPLSGEFLDTKDRQAEEDRQM
DTEAAASEAPQDVTYAQLHSLTLRREATEPPPSQEGPSPAVPSIYATLAIH

FIGURE 12

LILRB2, transcript variant 2:

MTPIVTVLICLGLSLGPRTHVQTGTIPKPTLWAEPDSVITQGSPVTLSCQGSLEAQE
YRLYREKKSASWITRIRPELVKNGQFHIPSITWEHTGRYGCQYYSRARWSELSDP
LVLVMTGAYPKPTLSAQPSPVVTSGGRVTLQCESQVAFGGFILCKEGEEEHPQCL
NSQPHARGSSRAIFSVGPVSPNRRWSHRCYGYDLNSPYVWSSPSDLLELLVPGVS
KKPSLSVQPGPVVAPGESLTLQCVSDVGYDRFVLYKEGERDLRQLPGRQPQAGL
SQANFTLGPVSRSYGGQYRCYGAHNLSSECSAPSDPLDILITGQIRGTPFISVQPGP
TVASGENVTLLCQSWRQFHTFLLTKAGAADAPLRLRSIHEYPKYQAEFPMSPVTS
AHAGTYRCYGSLNSDPYLLSHPSEPLELVVSGPSMGSSPPPTGPISTPGPEDQPLTP
TGSDPQSGLGRHLGVVIGILVAVVLLLLLLLLLFLILRHRRQGKHWTSTQRKADF
QHPAGAVGPEPTDRGLQWRSSPAADAQEENLYAAVKDTQPEDGVEMDTRAAA
SEAPQDVTYAQLHSLTLRRKATEPPPSQEREPPAEPSIYATLAIH*

FIGURE 13

LILRB3, transcript variant 1:

MTPALTALLCLGLSLGPRTRVQAGPFPKPTLWAEPGSVISWGSPVTIWCQGSQEA
QEYRLHKEGSPEPLDRNNPLEPKNKARFSIPSMTEHHAGRYRCHYYSSAGWSEPS
DPLEMVMTGAYSKPTLSALPSPVVASGGNMTLRCGSQKGYHHFVLMKEGEHQL
PRTLDSQQLHSRGFQALFPVGPVTPSHRWRFTCYYYYTNTPWVWSHPSDPLEILP
SGVSRKPSLLTLQGPVLAPGQSLTLQCGSDVGYNRFVLYKEGERDFLQRPGQQP
QAGLSQANFTLGPVSPSNGGQYRCYGAHNLSSEWSAPSDPLNILMAGQIYDTVS
LSAQPGPTVASGENVTLLCQSWWQFDTFLLTKEGAAHPPLRLRSMYGAHKYQA
EFPMSPVTSAHAGTYRCYGSYSSNPHLLSHPSEPLELVVSGHSGGSSLPPTGPPST
PGLGRYLEVLIGVSVAFVLLLFLLLFLLLRRQRHSKHRTSDQRKTDFQRPAGAAE
TEPKDRGLLRRSSPAADVQEENLYAAVKDTQSEDRVELDSQQSPHDEDPQAVTY
APVKHSSPRREMASPPSSLSGEFLDTKDRQVEEDRQMDTEAAASEASQDVTYAQ
LHSLTLRRKATEPPPSQEGEPPAEPSIYATLAIH

FIGURE 14

LILRB3, transcript variant 2:

MTPALTALLCLGLSLGPRTRVQAGPFPKPTLWAEPGSVISWGSPVTIWCQGSQEA
QEYRLHKEGSPEPLDRNNPLEPKNKARFSIPSMTEHHAGRYRCHYYSSAGWSEPS
DPLEMVMTGAYSKPTLSALPSPVVASGGNMTLRCGSQKGYHHFVLMKEGEHQL
PRTLDSQQLHSRGFQALFPVGPVTPSHRWRFTCYYYYTNTPWVWSHPSDPLEILP
SGVSRKPSLLTLQGPVLAPGQSLTLQCGSDVGYNRFVLYKEGERDFLQRPGQQP
QAGLSQANFTLGPVSPSNGGQYRCYGAHNLSSEWSAPSDPLNILMAGQIYDTVS
LSAQPGPTVASGENVTLLCQSWWQFDTFLLTKEGAAHPPLRLRSMYGAHKYQA
EFPMSPVTSAHAGTYRCYGSYSSNPHLLSHPSEPLELVVSGHSGGSSLPPTGPPST
PGLGRYLEVLIGVSVAFVLLLFLLLFLLLRRQRHSKHRTSDQRKTDFQRPAGAAE
TEPKDRGLLRRSSPAADVQEENLYAAVKDTQSEDRVELDSQSPHDEDPQAVTYA
PVKHSSPRREMASPPSSLSGEFLDTKDRQVEEDRQMDTEAAASEASQDVTYAQL
HSLTLRRKATEPPPSQEGEPPAEPSIYATLAIH

FIGURE 15

LILRB5, transcript variant 1:

MTLTLSVLICLGLSVGPRTCVQAGTLPKPTLWAEPASVIARGKPVTLWCQGPLET
EEYRLDKEGLPWARKRQNPLEPGAKAKFHIPSTVYDSAGRYRCYYETPAGWSEP
SDPLELVATGFYAEPTLLALPSPVVASGGNVTLQCDTLDGLLTFVLVEEEQKLPR
TLYSQKLPKGPSQALFPVGPVTPSCRWRFRCYYYYRKNPQVWSNPSDLLEILVPG
VSRKPSLLIPQGSVVARGGSLTLQCRSDVGYDIFVLYKEGEHDLVQGSGQQPQA
GLSQANFTLGPVSRHGGQYRCYGAHNLSPRWSAPSDPLDILIAGLIPDIPALSVQ
PGPKVASGENVTLLCQSWHQIDTFFFLTKEGAAHPPLCLKSKYQSYRHQAEFSMS
PVTSAQGGTYRCYSAIRSYPYLLSSPSYPQELVVSGPSGDPSLSPTGSTPTPAGPED
QPLTPTGLDPQSGLGRHLGVVTGVSVAFVLLLFLLLFLLLRHRHQSKHRTSAHFY
RPAGAAGPEPKDQGLQKRASPVADIQEEILNAAVKDTQPKDGVEMDARAAASE
APQDVTYAQLHSLTLRREATEPPPSQEREPPAEPSIYAPLAIH

FIGURE 16

LILRB5, transcript variant 2:

MTLTLSVLICLGLSVGPRTCVQAGTLPKPTLWAEPASVIARGKPVTLWCQGPLET
EEYRLDKEGLPWARKRQNPLEPGAKAKFHIPSTVYDSAGRYRCYYETPAGWSEP
SDPLELVATGFYAEPTLLALPSPVVASGGNVTLQCDTLDGLLTFVLVEEEQKLPR
TLYSQKLPKGPSQALFPVGPVTPSCRWRFRCYYYYRKNPQVWSNPSDLLEILVPG
VSRKPSLLIPQGSVVARGGSLTLQCRSDVGYDIFVLYKEGEHDLVQGSGQQPQA
GLSQANFTLGPVSRSHGGQYRCYGAHNLSPRWSAPSDPLDILIAGLIPDIPALSVQ
PGPKVASGENVTLLCQSWHQIDTFFLTKEGAAHPPLCLKSKYQSYRHQAEFSMS
PVTSAQGGTYRCYSAIRSYPYLLSSPSYPQELVVSGPSGDPSLSPTGSTPTPGPEDQ
PLTPTGLDPQSGLGRHLGVVTGVSVAFVLLLFLLLFLLLRHRHQSKHRTSAHFYR
PAGAAGPEPKDQGLQKRASPVADIQEEILNAAVKDTQPKDGVEMDARAAASEA
PQDVTYAQLHSLTLRREATEPPPSQEREPPAEPSIYAPLAIH

FIGURE 17

LILRB5, transcript variant 3:

MTLTLSVLICLGLSVGPRTCVQAGTLPKPTLWAEPASVIARGKPVTLWCQGPLET
EEYRLDKEGLPWARKRQNPLEPGAKAKFHIPSTVYDSAGRYRCYYETPAGWSEP
SDPLELVATGVSRKPSLLIPQGSVVARGGSLTLQCRSDVGYDIFVLYKEGEHDLV
QGSGQQPQAGLSQANFTLGPVSRSHGGQYRCYGAHNLSPRWSAPSDPLDILIAG
LIPDIPALSVQPGPKVASGENVTLLCQSWHQIDTFFLTKEGAAHPPLCLKSKYQSY
RHQAEFSMSPVTSAQGGTYRCYSAIRSYPYLLSSPSYPQELVVSGPSGDPSLSPTG
STPTPAGPEDQPLTPTGLDPQSGLGRHLGVVTGVSVAFVLLLFLLLFLLLRHRHQ
SKHRTSAHFYRPAGAAGPEPKDQGLQKRASPVADIQEEILNAAVKDTQPKDGVE
MDARAAASEAPQDVTYAQLHSLTLRREATEPPPSQEREPPAEPSIYAPLAIH

FIGURE 18

MODULATORS OF NEURONAL REGENERATION

This application claims priority under 35 U.S.C. 119(e) to Provisional Application No. 60/865,772 filed on Nov. 14, 2006 and Provisional Application No. 60/890,416 filed on Feb. 16, 2007, the entire disclosures of which are expressly incorporated by reference herein.

FIELD OF THE INVENTION

The present invention relates generally to neural development and neurological disorders. The invention specifically concerns identification of novel modulators of the myelin-associated inhibitory system and various uses of the modulators so identified.

BACKGROUND OF THE INVENTION

Myelin and Myelin-Associated Proteins

It is known that axons of the adult mammalian CNS neurons have very limited capacity to regenerate following injury, whereas axons in the peripheral nervous system (PNS) regenerate rapidly. CNS neuron's limited capacity to regenerate is in part an intrinsic property of CNS axons, but also due to an impermissible environment. The CNS myelin, while it is not the only source of inhibitory cues for neurite growth, contains numerous inhibitory molecules that actively block axonal growth and therefore constitutes a significant barrier to regeneration. Three of such myelin-associated proteins (MAPs) have been identified: Nogo (also known as NogoA) is a member of the Reticulon family of proteins having two transmembrane domains; myelin-associated glycoprotein (MAG) is a transmembrane protein of the Ig superfamily; and OMgp is a leucine rich repeat (LRR) protein with a glycosylphosphatidylinositol (GPI) anchor. Chen et al., Nature 403:434-39 (2000); GrandPre et al., Nature 417:439-444 (2000); Prinjha et al., Nature 403:383-384 (2000); McKerracher et al, Neuron 13:805-11 (1994); Wang et al, Nature 417:941-4 (20020: Kottis et al J. Neurochem 82:1566-9 (2002). A portion of NogoA, Nogo66, has been described as a 66-amino acid extracellular polypeptide that is found in all three isoforms of Nogo.

Despite their structural differences, all three inhibitory proteins (also Nogo66) have been shown to bind the same GPI-anchored receptor, called Nogo receptor (NgR; also known as Nogo Receptor-1 or NgR1), and it has been proposed that NgR might be required for mediating the inhibitory actions of Nogo, MAG and OMgp. Fournier et al., Nature 409:34-346 (2001). Two NgR1 homologs (NgR2 and NgR3) have also been identified. US 2005/0048520 A1 (Strittmatter et al.), published Mar. 3, 2005. Given that NgR is a GPI-anchored cell surface protein, it is unlikely to be a direct signal transductor (Zheng et al., Proc. Natl. Acad. Sci. USA 102:1205-1210 (2005)). Others have suggested that the neurotrophin receptor p75$^{NTR}$ acts as a co-receptor for NgR and provides the signal-transducing moiety in a receptor complex (Wang et al., Nature 420:74-78 (2002); Wong et al., Nat. Neurosci. 5:1302-1308 (2002)).

However, recent studies of the NgR/p75$^{NTR}$ receptor complex have raised questions about NgR's role in the myelin-associated inhibitory system. Zheng et al. have shown that genetic deletion of NgR does not reduce neurite inhibition in vitro or promote corticospinal tract (CST) regeneration in vivo. Zheng et al. (2005), supra. Consistent with these results, another study failed to detect any enhanced regeneration of the CST in NgR mutant mice. Kim et al., Neuron 44:439-451 (2004). These findings contradict the hypothesis that the NgR/p75$^{NTR}$ receptor complex represents the key converging point for multiple inhibitory signals. The failure of CST regeneration in NgR mutant mice contrasts with the CST regeneration observed with wild-type animals treated with a peptide antagonist of the Nogo66/NgR interaction (GrandPre et al. Nature 417:5470551 (2002) and Li and Strittmatter, Nature 23:4219-4227 (2002)). Another study has shown that expression of a dominant-negative fragment of NgR lead to enhanced regeneration of optic nerve axons in combination with a conditional injury. Both these experiments failed to test directly the involvement of NgR, as both antagonistic peptides have the potential to interfere with other inhibitory ligands/receptors.

These inconsistencies with the experimental results are a strong indication that NgR, or the NgR/p75$^{NTR}$ receptor complex, might play a limited role in the myelin associated inhibition of CNS regeneration, and other components, such as additional receptors or binding partners might participate in transmitting the inhibitory signal.

PirB and Human Orthologs

The major histocompatibility complex (MHC) class I was originally identified as a region encoding a family of molecules that are important for the immune system. Recent evidences have indicated that MHC class I molecules have additional functions in the development and adult CNS. Boulanger and Shatz, Nature Rev Neurosci. 5:521-531 (2004); US 2003/0170690 (Shatz and Syken), published Sep. 11, 2003. Many of the MHC class I members and their binding partners are found to be expressed in CNS neurons. Recent genetic and molecular studies have focused on the physiological functions of CNS MHC class I, and the initial results suggested that MHC class I molecules might be involved in activity-dependent synaptic plasticity, a process during which the strength of existing synaptic connections increases or decreases in response to neuronal activity, followed by long term structural alterations to circuits. Moreover, the MHC class I encoding region has also been genetically linked to a wide variety of disorders with neurological symptoms, and abnormal functions of MHC class I molecules are thought to contribute to the disruption of normal brain development and plasticity.

One of the known MHC class I receptors in the immune setting is PirB, a murine polypeptide that was first described by Kubagawa et al., Proc. Nat. Acad. Sci. USA 94:5261-6 (1997). Mouse PirB has several human orthologs, which are members of the leukocyte immunoglobulin-like receptor, subfamily B (LILRB), and are also referred to as "immunoglobulin-like transcripts" (ILTs). The human orthologs show significant homology to the murine sequence, from highest to lowest in the following order: LILRB3/ILT5, LILRB 1/ILT2, LILRB5/ILT3, LILRB2/ILT4, and, just as PirB, are all inhibitory receptors. LILRB3/ILT5 (NP_006855) and LILRB1/ILT2 (NP_006660) were first described by Samaridis and Colonna, Eur. J. Immunol. 27(3):660-665 (1997). LILRB5/ILT3 (NP_006831) has been identified by Borges et al., J. Immunol. 159(11):5192-5196 (1997). LILRB2/ILT4 (also known as MIR10), was identified by Colonna et al., J. Exp. Med. 186:1809-18 (1997). PirB and its human orthologs show a great degree of structural variability. The sequences of various alternatively spliced forms are available from EMBL/GenBank, including, for example, the following accession numbers for human ILT4 cDNA: ILT4-c11 AF009634; ILT4-c117 AF11566; ILT4-c126 AF11565. As noted above, the PirB/LILRB polypeptides are MHC Class I (MHCI) inhibitory receptors, and are known for their role in regulating immune cell activation (Kubagawa et al., supra; Hayami et al., *J. Biol. Chem.* 272:7320 (1997); Takai et al., *Immunology* 115:433 (2005); Takai et al., *Immunol. Rev.* 181:215 (2001); Nakamura et al. *Nat. Immunol.* 5:623 (2004); Liang et al., *Eur. J. Immunol.* 32:2418 (2002)).

A recent study by Syken et al. (*Science* 313:1795-800 (2006)) reported that PirB is expressed in subsets of neurons throughout the brain. In mutant mice lacking functional PirB, cortical ocular dominance (OD) plasticity is significantly enhanced at all ages, suggesting PirB's function in restricting activity-dependent plasticity in visual cortex.

The present invention is based, at least in part, on the surprising finding that PirB/LILRB are binding partners for Nogo (Nogo66) and MAG, and that PirB/LILRB antagonists and reduced PirB/LILRB activity effectively disrupt the myelin-associated inhibitory pathway, thereby promoting neuronal regeneration.

SUMMARY OF THE INVENTION

In one aspect, the invention concerns a method for identifying a PirB/LILRB antagonist comprising contacting a candidate agent with a receptor complex comprising PirB/LILRB and myelin or a myelin-associated protein, or a fragment thereof, and detecting the ability of the candidate agent to inhibit the interaction between PirB/LILRB and the myelin-associated protein, or fragment thereof, wherein the candidate agent is identified as an antagonist if the interaction is inhibited.

In one embodiment, the interaction detected is binding.

In another embodiment, the interaction detected is cellular signaling.

In a further embodiment, the cellular signaling results in the inhibition of axonal outgrowth or neuronal regeneration.

In a still further embodiment, the myelin-associated protein is selected from the group consisting of Nogo, MAG, OMgp, and fragments thereof.

In another embodiment, PirB/LILRB is a human LILRB protein, such as LILRB1, LILRB2, LILRB3, or LILRB5.

In certain specific embodiments, PirB/LILRB is selected from the group consisting of LILRB2, transcript variant 1 (SEQ ID NO: 2), LILRB2, transcript variant 2 (SEQ ID NO: 14), LILRB 1, transcript variant 1 (SEQ ID NO: 10), LILRB 1, transcript variant 2 (SEQ ID NO: 11), LILRB1, transcript variant 3 (SEQ ID NO: 12), LILRB1, transcript variant 4 (SEQ ID NO: 13), LILRB3, transcript variant 1 (SEQ ID NO: 15), LILRB3, transcript variant 2 (SEQ ID NO: 16), LILRB5, transcript variant 1 (SEQ ID NO: 17). LILRB5, transcript variant 2 (SEQ ID NO: 18), and LILRB5, transcript variant 3 (SEQ ID NO: 19).

In an additional embodiment, receptor complex further comprises NgR.

In different embodiments, the candidate agent is selected from the group consisting of antibodies, polypeptides, peptides, nucleic acids, small organic molecules, polysaccharides and polynucleotides, and preferably is an antibody or a short-interfering RNA (siRNA). The antibody preferably specifically binds PirB/LILRB, such as LILRB2, and includes, without limitation, chimeric, humanized, human antibody and antibody fragments.

In a particular embodiment, the antibody fragment is elected from the group consisting of Fv, Fab, Fab', and F(ab')$_2$ fragments.

In a further embodiment, at least one of PirB/LILRB and the myelin or myelin-associated protein, or fragment thereof, is immobilized.

In a still further embodiment, the assay is a cell-based assay.

In a particular embodiment, the cell-based assay comprises culturing neuronal cells with the myelin or myelin-associated protein, of fragment thereof, in the presence and absence of a candidate agent and determining the change in neurite length, wherein the candidate agent is identified as an antagonist when the neurite length is longer in the presence of the candidate agent.

In the cell-based assay above, the neuronal cells may be primary neurons, or may, for example, be derived from cells or cell lines, including stem cells, e.g. embryonic stem (ES) cells. In other embodiments, the neurons may, for example, be selected from the group consisting of cerebellar granule neurons, dorsal root ganglion neurons, and cortical neurons.

In one embodiment, the methods described above further comprise the step of using the antagonist identified to enhance neurite outgrowth, and/or promoting neuronal growth, repair and/or regeneration.

In another embodiment, the methods described above further comprise the step of administering the antagonist identified to a subject with a disease or condition benefiting from the enhancement of neurite outgrowth, promotion of neuronal growth, repair or regeneration. Such disease or condition may, for example, be a neurological disorder, which may be characterized by a physically damaged nerve, or may be selected from the group consisting of peripheral nerve damage caused by physical injury, diabetes; physical damage to the central nervous system; brain damage associated with stroke, trigeminal neuralgia, glossopharyngeal neuralgia, Bell's Palsy, myasthenia gravis, muscular dystrophy, amyotrophic lateral sclerosis (ALS), progressive muscular atrophy, progressive bulbar inherited muscular atrophy, herniated, ruptured and prolapsed invertebrate disk syndromes, cervical spondylosis, plexus disorders, thoracic outlet destruction syndromes, peripheral neuropathies, prophyria, Gullain-Barre syndrome, Alzheimer's disease, Huntington's Disease, and Parkinson's disease.

In another aspect, the invention concerns an agent identified by any one of the methods herein.

In an embodiment, the agent is selected from the group consisting of antibodies, polypeptides, peptides, nucleic acids, small organic molecules, polysaccharides and polynucleotides, and preferably is an antibody or a short-interfering RNA (siRNA).

In a further aspect, the invention concerns a composition comprising an agent identified by the methods herein for stimulation of neuronal regeneration.

In a still further aspect, the invention concerns a kit comprising an agent identified by the methods herein and instructions for neuronal regeneration.

In yet another aspect, the invention concerns use of a complex of PirB/LILRB and myelin or a myelin-associated protein, or a fragment thereof, to identify a PirB/LILRB antagonist.

In a different aspect, the invention concerns use of a PirB/LILRB antagonist in the preparation of a medicament for the treatment of a disease or condition benefiting from the enhancement of neurite outgrowth, promotion of neuronal growth, repair or regeneration. In another aspect, the invention concerns use of a PirB/LILRB antagonist in the preparation of a medicament for the treatment of a neurological disorder, where the neurological disorder may be characterized by a physically damaged nerve, or may be selected, for example, from the group consisting of peripheral nerve damage caused by physical injury, diabetes; physical damage to the central nervous system; brain damage associated with stroke, trigeminal neuralgia, glossopharyngeal neuralgia, Bell's Palsy, myasthenia gravis, muscular dystrophy, amyotrophic lateral sclerosis (ALS), progressive muscular atrophy, progressive bulbar inherited muscular atrophy, herniated, ruptured and prolapsed invertebrate disk syndromes, cervical spondylosis, plexus disorders, thoracic outlet destruction syndromes, peripheral neuropathies, prophyria, Gullain-Barre syndrome, Alzheimer's disease, Huntington's Disease, and Parkinson's disease.

In a further aspect, the invention concerns a PirB/LILRB antagonist for use in the treatment of a disease or condition benefiting from the enhancement of neurite outgrowth, promotion of neuronal growth, repair or regeneration.

In a still further aspect, the invention concerns a PirB/LILRB antagonist for use in the treatment of a neurological disorder, where the neurological disorder is as discussed above.

BRIEF DESCRIPTION OF THE DRAWINGS

FIG. 5 shows the mouse PirB amino acid sequence (SEQ ID NO: 1) and a human LILRB2, transcript variant 1 amino acid sequence (SEQ ID NO: 2).

FIG. 9 shows the amino acid sequence of LILRB1, transcript variant 1 (SEQ ID NO: 10).

FIG. 10 shows the amino acid sequence of LILRB1, transcript variant 2 (SEQ ID NO: 11).

FIG. 11 shows the amino acid sequence of LILRB1, transcript variant 3 (SEQ ID NO: 12).

FIG. 12 shows the amino acid sequence of LILRB1, transcript variant 4 (SEQ ID NO: 13).

FIG. 13 shows the amino acid sequence of LILRB2, transcript variant 2 (SEQ ID NO: 14).

FIG. 14 shows the amino acid sequence of LILRB3, transcript variant 1 (SEQ ID NO: 15).

FIG. 15 shows the amino acid sequence of LILRB3, transcript variant 2 (SEQ ID NO: 16).

FIG. 16 shows the amino acid sequence of LILRB5, transcript variant 1 (SEQ ID NO: 17).

FIG. 17 shows the amino acid sequence of LILRB5, transcript variant 2 (SEQ ID NO: 18).

FIG. 18 shows the amino acid sequence of LILRB5, transcript variant 3 (SEQ ID NO: 19).

DETAILED DESCRIPTION OF THE INVENTION

A. Definitions

Figure 1:
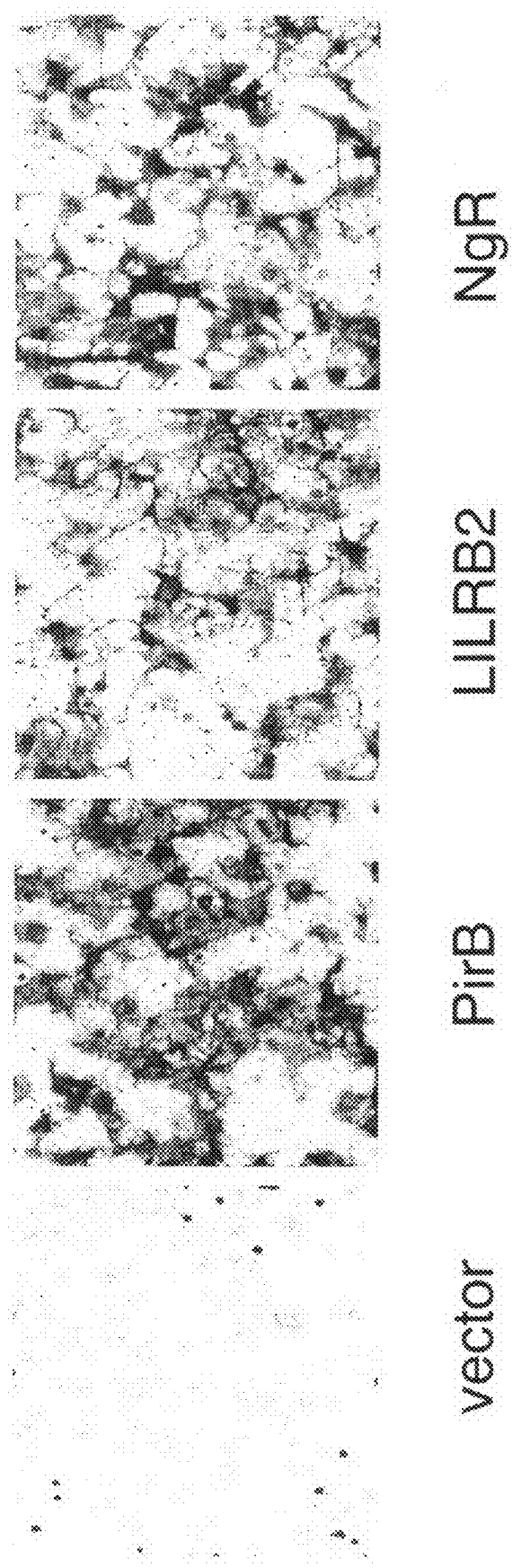
FIG. 1 shows Alkaline Phosphatase activity on transfected COS cells following incubation with AP-Nogo66. AP-Nogo66 binds PirB and LILRB2.

The terms "paired-immunoglobulin-like receptor B" and "PirB" are used herein interchangeably, and refer to a native-sequence, 841-amino acid mouse inhibitory protein of SEQ ID NO: 1 (FIG. 5) (NP_035225), and its native-sequence homologues in rat and other non-human mammals, including all naturally occurring variants, such as alternatively spliced transcript variants and allelic variants and isoforms, as well as soluble forms thereof.

The terms "LILRB," "ILT" and "MIR," are used herein interchangeably, and refer to all members of the human "leukocyte immunoglobulin-like receptor, subfamily B", including all naturally occurring variants, such as alternatively spliced transcript variants and allelic variants and isoforms, as well as soluble forms thereof. Individual members within this family are designated by numbers following the acronym, such as, for example, LILRB3/ILT5, LILRB1/LT2, LILRB5/ILT3, and LILRB2/ILT4, where a reference to any individual member, unless otherwise noted, also includes reference to all naturally occurring variants, such as alternatively spliced transcript variants and allelic variants and isoforms, as well as soluble forms thereof. Thus, for example, "LILRB1" is used herein to specifically include transcript variants 1-4 (SEQ ID NOs: 10, 11, 12, and 13, shown in FIGS. 9-12), as well as all other naturally occurring variants, such as other alternatively spliced transcript variants, allelic variants and isoforms, and soluble forms thereof. The term "LILRB2" is used herein to specifically include LILRB2, transcript variant 1 (SEQ ID NO: 2, shown in FIG. 5) and transcript variant 2 (SEQ ID NO: 14, shown in FIG. 13), as well as all other naturally occurring variants, such as other alternatively spliced transcript variants, allelic variants and isoforms, and soluble forms thereof. The term "LILRB3" is used herein to specifically include LILRB3, transcript variant 1 (SEQ ID NO: 15, shown in FIG. 14) and transcript variant 2 (SEQ ID NO: 16, shown in FIG. 15), as well as all other naturally occurring variants, such as other alternatively spliced transcript variants, allelic variants and isoforms, and soluble forms thereof. The term "LILRB5" specifically includes transcript variants 1-3 (SEQ ID NOs: 17-19, shown in FIGS. 16-18), as well as all other naturally occurring variants, such as other alternatively spliced transcript variants, allelic variants and isoforms, and soluble forms thereof.

The term "PirB/LILRB" is used herein as a short-hand description to refer to any of the individual mouse PirB and human LILRB proteins and native sequence homologues in other non-human mammals, including all naturally occurring variants, such as alternatively spliced transcript and allelic variants and isoforms, as well as soluble forms thereof.

The term "myelin-associated protein" is used in the broadest sense and includes all proteins present in CNS myelin that inhibit neuronal regeneration, including Nogo, MAG and OMgp.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS- PAGE under non-reducing or reducing conditions using Coomassie blue or, preferably, silver stain, or (3) to homogeneity by mass spectroscopic or peptide mapping techniques. Isolated protein includes protein in situ within recombinant cells, since at least one component of the natural environment of the protein in question will not be present. Ordinarily, however, isolated protein will be prepared by at least one purification step.

An "isolated" nucleic acid molecule is a nucleic acid molecule that is identified and separated from at least one contaminant nucleic acid molecule with which it is ordinarily associated in the natural source of the nucleic acid in question. An isolated nucleic acid molecule is other than in the form or setting in which it is found in nature. Isolated nucleic acid molecules therefore are distinguished from the nucleic acid molecules as they exist in natural cells. However, an isolated nucleic acid molecule includes nucleic acid molecules contained in cells that ordinarily express such nucleic acid where, for example, the nucleic acid molecule is in a chromosomal location different from that of natural cells.

As used herein, the term "PirB/LILRB antagonist" is used to refer to an agent capable of blocking, neutralizing, inhibiting, abrogating, reducing or interfering with PirB/LILRB activities. Particularly, the PirB/LILRB antagonist interferes with myelin associated inhibitory activities, thereby enhancing neurite outgrowth, and/or promoting neuronal growth, repair and/or regeneration. In a preferred embodiment, the PirB/LILRB antagonist inhibits the binding of PirB/LILRB to Nogo66 and/or MAG and/or OMgp by binding to PirB/LILRB. PirB/LILRB antagonists include, for example, antibodies to PirB/LILRB and antigen binding fragments thereof, truncated or soluble fragments of PirB/LILRB, Nogo 66, MAG or OMgp that are capable of sequestering the binding between PirB/LILRB and Nogo 66, or between PirB/LILRB and MAG, or between PirB/LILRB and OMgp and small molecule inhibitors of the PirB/LILRB related inhibitory pathway. PirB/LILRB antagonists also include short-interfering RNA (siRNA) molecules capable of inhibiting or reducing the expression of PirB/LILRB mRNA.

The term "antibody" herein is used in the broadest sense and specifically covers intact antibodies, monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

Antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 (1984)). Chimeric antibodies of interest herein include primatized antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains (Fab, Fab', F(ab')$_2$, Fabc, Fv), in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the regions of an antibody variable domain which are hypervariable in sequence and/or form structurally defined loops. The hypervariable region comprises amino acid residues from a "complementarity determining region" or "CDR" (i.e. residues 24-34, 50-56, and 89-97 in the light chain variable domain and 31-35, 50-65, and 95-102 in the heavy chain variable domain; Kabat et al., *Sequences of Pro-* teins of Immunological Interest, 5th Ed. Public Health Service, National Institutes of Health, Bethesda, Md. (1991)) and/or those residues from a "hypervariable loop" (i.e. residues 26-32, 50-52, and 91-96 in the light chain variable domain and 26-32, 53-55, and 96-101 in the heavy chain variable domain; Chothia and Lesk J. Mol. Biol. 196:901-917 (1987)). In both cases, the variable domain residues are numbered according to Kabat et al., supra, as discussed in more detail below. "Framework" or "FR" residues are those variable domain residues other than the residues in the hypervariable regions as herein defined.

A "parent antibody" or "wild-type" antibody is an antibody comprising an amino acid sequence which lacks one or more amino acid sequence alterations compared to an antibody variant as herein disclosed. Thus, the parent antibody generally has at least one hypervariable region which differs in amino acid sequence from the amino acid sequence of the corresponding hypervariable region of an antibody variant as herein disclosed. The parent polypeptide may comprise a native sequence (i.e. a naturally occurring) antibody (including a naturally occurring allelic variant), or an antibody with pre-existing amino acid sequence modifications (such as insertions, deletions and/or other alterations) of a naturally occurring sequence. Throughout the disclosure, "wild type," "WT," "wt," and "parent" or "parental" antibody are used interchangeably.

As used herein, "antibody variant" or "variant antibody" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. The antibody variant is generally one which comprises one or more amino acid alterations in or adjacent to one or more hypervariable regions thereof.

An "amino acid alteration" refers to a change in the amino acid sequence of a predetermined amino acid sequence. Exemplary alterations include insertions, substitutions and deletions. An "amino acid substitution" refers to the replacement of an existing amino acid residue in a predetermined amino acid sequence; with another different amino acid residue.

A "replacement" amino acid residue refers to an amino acid residue that replaces or substitutes another amino acid residue in an amino acid sequence. The replacement residue may be a naturally occurring or non-naturally occurring amino acid residue.

An "amino acid insertion" refers to the introduction of one or more amino acid residues into a predetermined amino acid sequence. The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence which does not exist in nature. An amino acid alteration "adjacent a hypervariable region" refers to the introduction or substitution of one or more amino acid residues at the N-terminal and/or C-terminal end of a hypervariable region, such that at least one of the inserted or replacement amino acid residue(s) form a peptide bond with the N-terminal or C-terminal amino acid residue of the hypervariable region in question.

A "naturally occurring amino acid residue" is one encoded by the genetic code, generally selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val).

A "non-naturally occurring amino acid residue" herein is an amino acid residue other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

Throughout this disclosure, reference is made to the numbering system from Kabat, E. A., et al., Sequences of Proteins of Immunological Interest (National Institutes of Health, Bethesda, Md. (1987) and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. The Kabat numbering scheme is followed in this description. For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program. Alignment may be facilitated by using some amino acid residues which are common to most Fab sequences. For example, the light and heavy chains each typically have two cysteines which have the same residue numbers; in $V_L$ domain the two cysteines are typically at residue numbers 23 and 88, and in the $V_H$ domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues (see, e.g. residues 100 abc in FIG. 1B). For candidate sequences which, for example, align with a Kabat sequence for residues 34 and 36 but have no residue between them to align with residue 35, the number 35 is simply not assigned to a residue.

As used herein, an antibody with a "high-affinity" is an antibody having a $K_D$, or dissociation constant, in the nanomolar (nM) range or better. A $K_D$ in the "nanomolar range or better" may be denoted by X nM, where X is a number less than about 10.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

The term "short-interfering RNA (siRNA)" refers to small double-stranded RNAs that interfere with gene expression. siRNAs are an intermediate of RNA interference, the process double-stranded RNA silences homologous genes. siRNAs typically are comprised of two single-stranded RNAs of about 15-25 nucleotides in length that form a duplex, which may include single-stranded overhang(s). Processing of the double-stranded RNA by an enzymatic complex, for example by polymerases, results in the cleavage of the double-stranded RNA to produce siRNAs. The antisense strand of the siRNA is used by an RNA interference (RNAi) silencing complex to guide mRNA cleavage, thereby promoting mRNA degradation. To silence a specific gene using siRNAs, for example in a mammalian cell, the base pairing region is selected to avoid chance complementarity to an unrelated mRNA. RNAi silencing complexes have been identified in the art, such as, for example, by Fire et al., *Nature* 391:806-811 (1998) and McManus et al., *Nat. Rev. Genet.* 3(10):737-47 (2002).

The term "interfering RNA (RNAi)" is used herein to refer to a double-stranded RNA that results in catalytic degradation of specific mRNAs, and thus can be used to inhibit/lower expression of a particular gene.

The term "polymorphism" is used herein to refer to more than one forms of a gene or a portion (e.g., allelic variant) thereof. A portion of a gene of which there are at least two different forms is referred to as a "polymorphic region" of the gene. A specific genetic sequence at a polymorphic region of a gene is an "allele." A polymorphic region can be a single nucleotide, which differs in different alleles, or can be several nucleotides long.

As used herein, the term "disorder" in general refers to any condition that would benefit from treatment with the compounds of the present invention, including any disease or disorder that can be treated by effective amounts of antagonists of PirB/LILRB. Non-limiting examples of disorders to be treated herein include, without limitation, diseases and conditions benefiting from the enhancement of neurite outgrowth, promotion of neuronal growth, repair or regeneration, including neurological disorders, such as physically damaged nerves and neurodegenerative diseases. Such disorders specifically include peripheral nerve damage caused by physical injury or disease states such as diabetes; physical damage to the central nervous system (spinal cord and brain); brain damage associated with stroke; and neurological disorders relating to neurodegeneration, such as, for example, trigeminal neuralgia, glossopharyngeal neuralgia, Bell's Palsy, myasthenia gravis, muscular dystrophy, amyotrophic lateral sclerosis (ALS), progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathies such as those caused by lead, dapsone, ticks, prophyria, Gullain-Barre syndrome, Alzheimer's disease, Huntington's Disease, or Parkinson's disease.

The terms "treating", "treatment" and "therapy" as used herein refer to curative therapy, prophylactic therapy, and preventative therapy. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature.

The term "preventing neurodegeneration," as used herein includes (1) the ability to inhibit or prevent neurodegeneration in patients newly diagnosed as having a neurodegenerative disease or at risk of developing a new neurodegenerative disease and (2) the ability to inhibit or prevent further neurodegeneration in patients who are already suffering from, or have symptoms of, a neurodegenerative disease.

The term "mammal" as used herein refers to any mammal classified as a mammal, including humans, higher non-human primates, rodents, domestic and farm animals, such as cows, horses, dogs and cats. In a preferred embodiment of the invention, the mammal is a human.

Administration "in combination with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. The term "progeny" refers to any and all offspring of every generation subsequent to an originally transformed cell or cell line. Mutant progeny that have the same function or biological activity as screened for in the originally transformed cell are included. Where distinct designations are intended, it will be clear from the context.

"Percent (%) amino acid sequence identity" with respect to the sequences identified herein is defined as the percentage of amino acid residues in a candidate sequence that are identical with the amino acid residues in a reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the US Copyright Office, Washington, D.C., 20559, registered under the US Copyright Registration No. TXU510087. The ALIGN-2 program is publicly available through Genentech, Inc., South San Francisco, Calif. All sequence comparison parameters are set by the ALIGN-2 program and do not vary.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"High stringency conditions", as defined herein, are identified by those that: (1) employ low ionic strength and high temperature for washing; 0.015 M sodium chloride/0.0015 M sodium citrate/0.1% sodium dodecyl sulfate at 50° C.; (2) employ during hybridization a denaturing agent; 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "small molecule" is defined herein to have a molecular weight below about 1000 Daltons, preferably below about 500 Daltons.

B. Screening Assays to Identify Stimulators of Neuronal Regeneration

The primary assays of the present invention are at least in part based on the recognition that PirB/LILRB is a receptor of the myelin proteins Nogo (Nogo66) and MAG, and that PirB/LILRB antagonists, which interfere with the association of PirB/LILRB with Nogo and/or MAG, are capable of enhancing neurite outgrowth, and/or promoting neuronal growth, repair and/or regeneration. In brief, such agents will be referred to herein as stimulators of neuronal regeneration.

Screening assays for antagonist drug candidates may be designed to identify compounds that bind or complex with PirB/LILRB, or otherwise interfere with the interaction of PirB/LILRB with Nogo, MAG or other members of the myelin-associated inhibitory system. The screening assays provided herein include assays amenable to high-throughput screening of chemical libraries, making them suitable for identifying small molecule drug candidates. Generally, binding assays and activity assays are provided.

The assays can be performed in a variety of formats, including, without limitation, protein-protein binding assays, biochemical screening assays, immunoassays, and cell-based assays, which are well characterized in the art.

All assays for antagonists are common in that they call for contacting the drug candidate with a PirB/LILRB polypeptide under conditions and for a time sufficient to allow these two components to interact.

In binding assays, the interaction is binding, and the complex formed can be isolated or detected in the reaction mixture. In a particular embodiment, either the PirB/LILRB polypeptide or the drug candidate is immobilized on a solid phase, e.g., on a microtiter plate, by covalent or non-covalent attachments. Non-covalent attachment generally is accomplished by coating the solid surface with a solution of the PirB/LILRB polypeptide and drying. Alternatively, an immobilized antibody, e.g., a monoclonal antibody, specific for the PirB/LILRB polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide which interacts with but does not bind to PirB/LILRB, the interaction of PirB/LILRB with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989);

Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for 1-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of PirB/LILRB and other intra- or extracellular components, in particular Nogo or MAG can be tested as follows. Usually a reaction mixture is prepared containing PirB/LILRB and the intra- or extracellular component under conditions and for a time allowing for the interaction of the two products. To test the ability of a candidate compound to inhibit the interaction of PirB/LILRB and Nogo or MAG, the reaction is run in the absence and in the presence of the test compound. In addition, a placebo may be added to a third reaction mixture, to serve as positive control.

It is emphasized that the screening assays specifically discussed herein are for illustration only. A variety of other assays, which can be selected depending on the type of the antagonist candidates screened (e.g. polypeptides, peptides, non-peptide small organic molecules, nucleic acid, etc.) are well know to those skilled in the art and are equally suitable for the purposes of the present invention.

The assays herein may be used to screed libraries of compounds, including, without limitation, chemical libraries, natural product libraries (e.g. collections of microorganisms, animals, plants, etc.), and combinatorial libraries comprised of random peptides, oligonucleotides or small organic molecules. In a particular embodiment, the assays herein are used to screen antibody libraries, including, without limitation, naïve human, recombinant, synthetic and semi-synthetic antibody libraries. The antibody library can, for example, be a phage display library, including monovalent libraries, displaying on average one single-chain antibody or antibody fragment per phage particle, and multi-valent libraries, displaying, on average, two or more antibodies or antibody fragments per viral particle. However, the antibody libraries to be screened in accordance with the present invention are not limited to phage display libraries. Other display technique include, for example, ribosome or mRNA display (Mattheakis et al., *Proc. Natl. Acad. Sci. USA* 91:9022-9026 (1994); Hanes and Pluckthun, *Proc. Natl. Acad. Sci. USA* 94:4937-4942 (1997)), microbial cell display, such as bacterial display (Georgiou et al., *Nature Biotech.* 15:29-34 (1997)), or yeast cell display (Kieke et al., *Protein Eng.* 10:1303-1310 (1997)), display on mammalian cells, spore display, viral display, such as retroviral display (Urban et al., *Nucleic Acids Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)).

The results obtained in the primary binding/interaction assays herein can be confirmed in in vitro and/or in vivo assays of neuronal regeneration. Alternatively, in vitro and/or in vivo assays of neuronal regeneration may be used as primary assays to identify the PirB/LILRB antagonists herein.

In vitro assays of neurite outgrowth are well known in the art and are described, for example, Jin and Strittmatter, *J Neurosci* 17:6256-6263 (1997); Fournier et al., *Methods Enzymol.* 325:473-482 (2000); Zheng et al., *Neuron* 38:213-224 (2003); Wang et al., *Nature* 417:941-944 (2002), and Neumann et al., *Neuron* 34:885-893 (2002)). Kits for measuring and quantifying neurite outgrowth are commercially available. Thus, for example, CHEMICON's Neurite Outgrowth Assay Kit (Catalog number NS200), uses microporous filter technology for the quantitative testing of compounds that influence neurite formation and repulsion. With this system, it is possible to screen biological and pharmacological agents simultaneously, directly evaluate adhesion and guidance receptor functions responsible for neurite extension and repulsion, as well as the analysis of gene function in transfected cells. The microporous filter allows for biochemical separation and purification of neurites and cell bodies for detailed molecular analysis of protein expression, signal transduction processes and identification of drug targets that regulate neurite outgrowth or retraction processes.

In a typical protocol, primary neurons isolated from rodent neural tissue (including cerebellar granule neurons, dorsal root ganglion neurons, and cortical neurons) are cultured on 96-well tissue culture dishes coated with immobilized whole myelin or myelin associated proteins (e.g., Nogo66, MAG and/or OMgp). Following a defined time in culture, typically 24-48 hours, the neurons are fixed with 4% paraformaldehyde and stained with a neuronal marker (anti-class III b-Tubulin, Covance). Image acquisition and analysis are then performed using the ImageXpress automated imaging system (Molecular Devices). Data is analyzed for changes in maximal or total neurite length per neuron.

In vivo assays include animal models of various neurodegenerative diseases, such as spinal cord injury models, visual cortex plasticity models, and other models known in the art. Thus, regeneration and plasticity can be studied in models of plasticity following unilateral pyramidotomy and models or traumatic brain injury. Other models of neurodegeneration include mouse models of multiple sclerosis, such as experimental autoimmune encephalitis (EAE), models of amylotrophic lateral sclerosis (ALS), such as the SODI mutant mouse, transgenic animal models of Alzheimer's disease, and animal models of Parkinson's disease.

C. Making Antibodies Acting as Stimulators of Neuronal Regeneration

The antibodies identified by the binding and activity assays of the present invention can be produced by methods known in the art, including techniques of recombinant DNA technology.

i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1N=C=NR$, where R and $R_1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al, Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., Nature, 348: 552-554 (1990).

Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992). Human antibodies can also be derived from phage-display libraries (Hoogenboom et al, J. Mol. Biol., 227:381 (1991); Marks et al, J. Mol. Biol., 222:581-597 (1991); Vaughan et al. Nature Biotech 14:309 (1996)). Generation of human antibodies from antibody phage display libraries is further described below.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from $E.$ $coli$ and chemically coupled to form $F(ab')_2$ fragments (Carter et al., Bio/Technology 10:163-167 (1992)). In another embodiment as described in the example below, the $F(ab')_2$ is formed using the leucine zipper GCN4 to promote assembly of the $F(ab')_2$ molecule. According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Examples of BsAbs include those with one arm directed against PirB/LILRB and another arm directed against Nogo or MAG or OMgp. A further example of BsABs include those with one arm directed against PirB/LILRB and another arm directed against NgR.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991). According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can also be directly recovered from *E. coli*, and can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Effector Function Engineering

It may be desirable to modify the antibody of the invention with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor-activity may also be prepared using heterobifunctonal cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al Anti-Cancer Drug Design 3:219-230 (1989).

(viii) Antibody-Salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or V.sub.H region, or more than one such region, of the antibody. Alternatively, the epitope is taken from the CH2 domain of the Fc region and transferred to the CL region or VL region, or both, of the antibody fragment.

(ix) Other Covalent Modifications of Antibodies

Covalent modifications of antibodies are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Examples of covalent modifications are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

(x) Generation of Antibodies from Synthetic Antibody Phage Libraries

In a preferred embodiment, the invention provides a method for generating and selecting novel antibodies using a unique phage display approach. The approach involves generation of synthetic antibody phage libraries based on single framework template, design of sufficient diversities within variable domains, display of polypeptides having the diversified variable domains, selection of candidate antibodies with high affinity to target the antigen, and isolation of the selected antibodies.

Details of the phage display methods can be found, for example, WO03/102157 published Dec. 11, 2003, the entire disclosure of which is expressly incorporated herein by reference.

In one aspect, the antibody libraries used in the invention can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$. In some embodiments, a library is created by substitution of residues 95-100a with amino acids encoded by both DVK and NNK codon sets. An example of an oligonucleotide set that is useful for creating these substitutions comprises the sequence $(DVK)_6(NNK)$. In another embodiment, a library is created by substitution of at least residues 95-100a with amino acids encoded by both DVK and NNK codon sets. An example of an oligonucleotide set that is useful for creating these substitutions comprises the sequence $(DVK)_5(NNK)$. Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

(xi) Antibody Mutants

The novel antibodies generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-PirB/LILRB antibody mutant preferably has a binding affinity for PirB/LILRB which is at least about 10 fold stronger, preferably at least about 20 fold stronger, more preferably at least about 50 fold stronger, and sometimes at least about 100 fold or 200 fold stronger, than the binding affinity of the parent antibody.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mol. Biol.* 196:901-917); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened. Preferred Substitutions:

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |

| Original Residue | Exemplary Substitutions | Preferred Substitutions |
|---|---|---|
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

(xii) Recombinant Production of Antibodies

For recombinant production of an antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serrafia*, e.g., *Serratia marcescans*, and Shigeila, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida; Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed bySV40 (COS-7, ATCC CRL 1651); human embryonic kidney line (293 or 293 cells suclosed for growth in suspension culture, Graham et al, J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

D. Uses of Stimulators of Neuronal Regeneration

The molecules identified in the screening assays of the present invention are believed to find use as agents for enhancing the survival or inducing the outgrowth of nerve cells. They are, therefore, useful in the therapy of degenerative disorders of the nervous system ("neurodegenerative diseases"), including, for example, peripheral nerve damage caused by physical injury (e.g., burns, wounds) or disease states such as diabetes, kidney dysfunction or by the toxic effects of chemotherapeutics used to treat cancer and AIDS; physical damage to the central nervous system (spinal cord and brain); brain damage associated with stroke; and neurological disorders relating to neurodegeneration, such as, for example, trigeminal neuralgia, glossopharyngeal neuralgia, Bell's Palsy, myasthenia gravis, muscular dystrophy, amyotrophic lateral sclerosis (ALS), progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathies such as those caused by lead, dapsone, ticks, prophyria, Gullain-Barre syndrome, Alzheimer's disease, Huntington's Disease, or Parkinson's disease.

The compounds identified herein are also useful as components of culture media for use in culturing nerve cells in vitro.

Finally, preparations comprising compounds identified by the assays herein are useful as standards in competitive binding assays when labeled with radioiodine, enzymes, fluorophores, spin labels, and the like.

Therapeutic formulations of the compounds herein are prepared for storage by mixing the compound identified (such as an antibody) having the desired degree of purity with optional physiologically acceptable carriers, excipients or stabilizers (Remington's Pharmaceutical Sciences, supra), in the form of lyophilized cake or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Compounds to be used for in vivo administration must be sterile. This is readily accomplished by filtration through sterile filtration membranes, prior to or following lyophilization and reconstitution.

Therapeutic compositions may be placed into a container having a sterile access port, for example, an intravenous solution bag or vial having a stopper pierceable by a hypodermic injection needle.

The compounds identified by the assays of the present invention may be optionally combined with or administered in concert with neurotrophic factors including NGF, NT-3, and/or BDNF and used with other conventional therapies for degenerative nervous disorders.

The route of administration is in accord with known methods, e.g. injection or infusion by intravenous, intraperitoneal, intracerebral, intramuscular, intraocular, intraarterial or intralesional routes, topical administration, or by sustained release systems as noted below.

For intracerebral use, the compounds may be administered continuously by infusion into the fluid reservoirs of the CNS, although bolus injection is acceptable. The compounds are preferably administered into the ventricles of the brain or otherwise introduced into the CNS or spinal fluid. Administration may be performed by an indwelling catheter using a continuous administration means such as a pump, or it can be administered by implantation, e.g., intracerebral implantation, of a sustained-release vehicle. More specifically, the compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer patients and animal models for Parkinson's disease described by Harbaugh, *J. Neural Transm. Suppl.*, 24:271 (1987); and DeYebenes, et al., *Mov. Disord.* 2:143 (1987).

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., 1983, Biopolymers 22:547), poly (2-hydroxyethyl-methacrylate) (Langer, et al., 1981, J. Biomed. Mater. Res. 15:167; Langer, 1982, Chem. Tech. 12:98), ethylene vinyl acetate (Langer, et al., Id.) or poly-D-(−)-3-hydroxybutyric acid (EP 133,988A). Sustained release compositions also include liposomally entrapped compounds, which can be prepared by methods known per se. (Epstein, et al., *Proc. Natl. Acad. Sci.* 82:3688 (1985); Hwang, et al., *Proc. Natl. Acad. Sci. USA* 77:4030 (1980); U.S. Pat. Nos. 4,485,045 and 4,544,545; and EP 102,324A). Ordinarily the liposomes are of the small (about 200-800 Angstroms) unilamelar type in which the lipid content is greater than about 30 mol. % cholesterol, the selected proportion being adjusted for the optimal therapy.

An effective amount of an active compound to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer an active compound until a dosage is reached that repairs, maintains, and, optimally, reestablishes neuron function. The progress of this therapy is easily monitored by conventional assays.

Further details of the invention are illustrated by the following non-limiting examples.

Example 1

Expression Cloning LILRB2

To identify novel receptors for inhibitory myelin proteins, an expression cloning approach was taken. As bait, constructs were generated that fused Alkaline Phosphatase (AP) to the N- and/or C-terminus of the following characterized myelin inhibitors (human cDNA used): Nogo66, two additional inhibitory domains of NogoA (NiR<delta>D2 and NiG<delta>20) (Oertle T, *J Neurosci.* 2003, 23(13): 5393-406), MAG, and OMgp. These constructs were transfected into 293 cells to produce conditioned medium (in DMEM/2% FBS) containing the bait proteins. The cDNA library used in the screen was comprised of full-length human cDNA clones in expression-ready vectors generated by Origene. These cDNAs were compiled, arrayed, and pooled. Pools of approximately 100 cDNA's were transiently transfected into COS7 cells.

In particular, on Day 1, COS7 cells were plated at a density of 85,000 cells per well in 12-well plates. On Day 2, 1 mg of pooled cDNA's were transfected per well using the lipid-based transfection reagent FuGENE 6 (Roche). On Day 4, screening was performed. Briefly, culture medium was removed from cells and replaced with 0.5 ml of 293 cell-conditioned medium containing AP-fusion bait proteins (20-50 nM). Cells were incubated at room temperature for 90 minutes. The cells were then washed 3 times with phosphate-buffered saline (PBS), fixed for 7 minutes with 4% paraformaldehyde, washed 3 times in HEPES-buffered saline (HBS), and heat inactivated at 65° C. for 90 minutes to destroy endogenous AP activity. The cells were washed once in AP Buffer (100 mM NaCl, 5 mM $MgCl_2$, 100 mM Tris pH 9.5), and incubated in chromogenic substrate (Western Blue, Promega), and analyzed for presence of reaction product one hour after incubation, and again after overnight incubation. Positive cells were identified by the presence of dark blue precipitate over the surface of the membrane. Positive pools were further broken down to identify individual positive clones by subsequent rounds of screening.

From the screening, the following positive hits were identified:

MAG-AP bait yielded 4 positive hits. One was the previously characterized Nogo Receptor (Fournier et al., *Nature* 409, 342-346 (2001). Two of these hits were glycolytic processing enzymes, and deemed unlikely to be of relevance. The fourth was annotated as "*Homo sapiens* hypothetical protein from clone 643 (LOC57228), mRNA". Closer analysis of the cDNA revealed an alternative ORF that was homologous to the previously described protein SMAG.

AP-Nogo66 bait yielded 2 positive hits. One was the previously characterized Nogo Receptor. The other was "*Homo sapiens* leukocyte immunoglobulin-like receptor, subfamily B (with TM and ITIM domains), member 2 (LILRB2), mRNA" (SEQ ID NO: 2). This gene is also known by multiple alternative nomenclatures, including MIG10, ILT4, and LIR2 (Kubagawa et al., *Proc. Natl. Acad. Sci. USA* 94:5261-6 (1997); Colonna et al., *J. Exp. Med.* 186:1809-18 (1997)).

Example 2

AP-Nogo66 Binds PirB and LILRB2

To confirm Nogo66 binding to LILRB2 (SEQ ID NO: 2), and to test if Nogo66 binds to the murine orthologue PirB (SEQ ID NO: 1), binding assays similar to those described in Example 1 were carried out. Briefly, COS7 cells were transfected with cDNA's encoding PirB, LILRB2, or NgR as a positive control. 48 hours following transfection, cells were incubated with 293 cell-conditioned medium containing AP-Nogo66 for 90 minutes at RT. Cells were washed extensively, fixed, and endogenous AP activity was neutralized by heat inactivation. Cells were then reacted with chromogenic substrate (Western Blue, Promega).

As shown in FIG. 1, a strong positive signal was detected on both PirB- and LILRB2-expressing cells.

Example 3

MAG Binds PirB and LILRB2

To test whether or not MAG also binds to PirB and LILRB2, binding assays were performed with MAG-Fc, which is believed to be more bioactive than MAG-AP. COS7 cells were transfected with cDNA's encoding PirB, LILRB2, or mSMAGP as a positive control. 48 hours following transfection, cells were incubated with 293 cell-conditioned medium containing MAG-Fc for 90 minutes at RT. Cells were washed four times with Hank's Buffered Saline Solution (HBSS), fixed for five minutes with 2% paraformaldehyde, washed four times with HBSS, and blocked for 15 minutes with 10% heat-inactivated goat serum (HIGS) in HBSS. Cells were then incubated for one hour with anti-human Fc antibody (1:500, Jackson Immunochemicals), washed with 10% HIGS in PBS, and incubated with secondary antibody (AlexaFluor 568-conjugated goat anti-mouse, Molecular Probes). Cells were washed with PBS, coversliped, and immuno-fluorescence was detected using an inverted fluorescence microscope.

Figure 2:
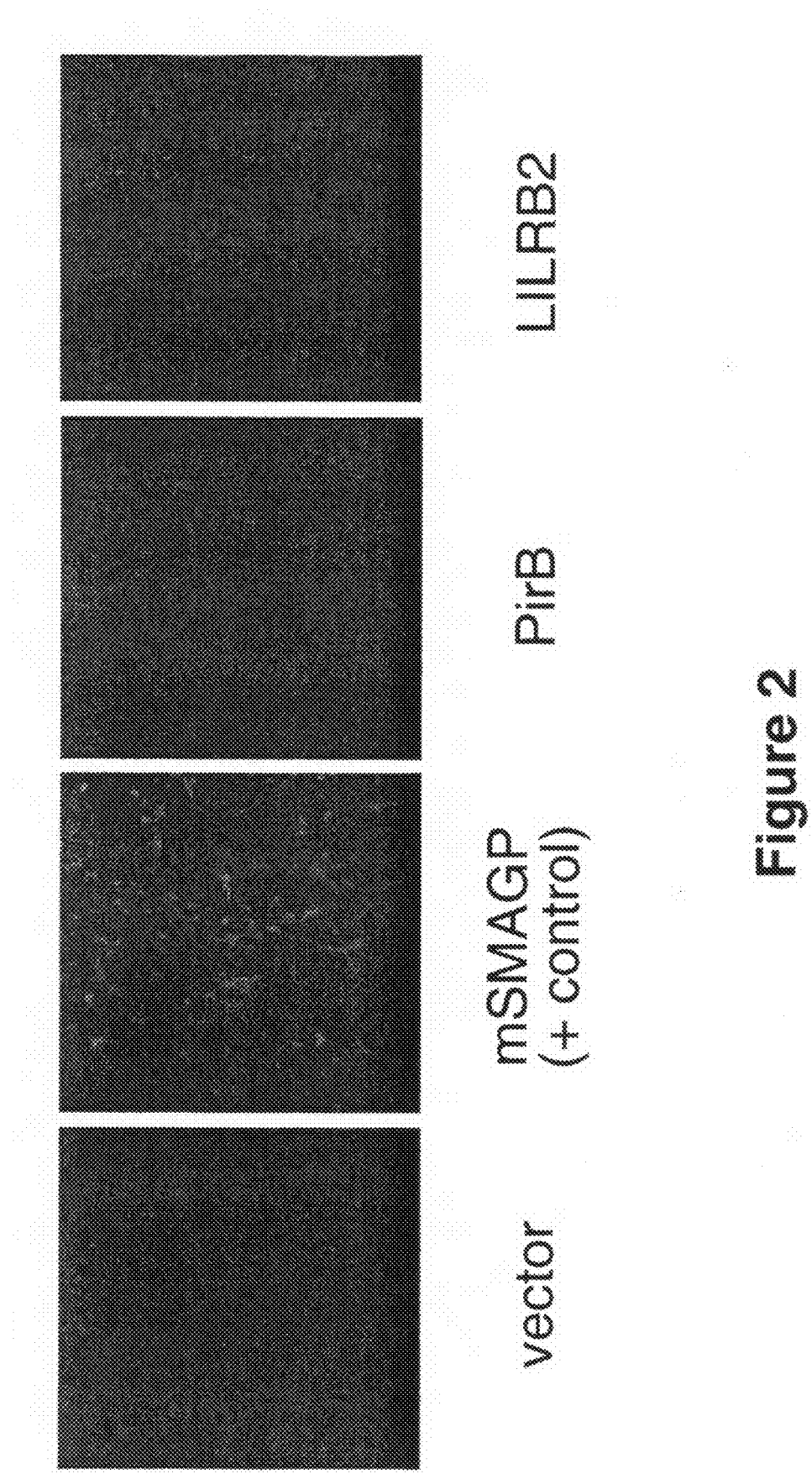
FIG. 2 shows immunoreactivity on transfected COS cells following incubation with MAG-Fc. MAG binds PirB and LILRB2.

The results are shown in FIG. 2. Compared to control cells, both PirB- and LILRB2-expressing cells show binding to MAG-Fc. In this example, mSMAGP-expressing cells served as a positive control for binding.

Example 4

PirbB is Expressed in the Nervous System

To address whether or not PirB is expressed in the nervous system, RT-PCR analysis was performed on mRNA isolated from different neural tissues. P7 cerebellum, P10 Dorsal Root Ganglia (DRG), adult brain, and adult spleen (positive control) were dissected from CD1 mice and immediately placed in RNAlater (Ambion). mRNA was extracted using the RNEasy isolation kit (Qiagen). cDNA was generated from mRNA using Invitrogen's Superscript III First Strand Synthesis system. RT-PCR was then performed using primers specific for PirB 5'TGAAGGCTCTCATTGGAGTGTCTG3' (SEQ ID NO: 20) and 5'GGCATAGGTCACATCCTGGGAC3' (SEQ ID NO: 3), primers cross-reactive with different members of the PirA subfamily (5'GTCTCAGAAACCATTGAATCC3' (SEQ ID NO: 4) and 5'GACAGAAAACTTTGGGTCAT-CAG3' (SEQ ID NO: 5)), or primers specific for mouse SMAGP (5'CCCTCAGCAACGATGAACAACC3' (SEQ ID NO: 6) and 5'TGGACCCTGGAGTCAGTGATTC3'(SEQ ID NO: 7)).

Figure 3:
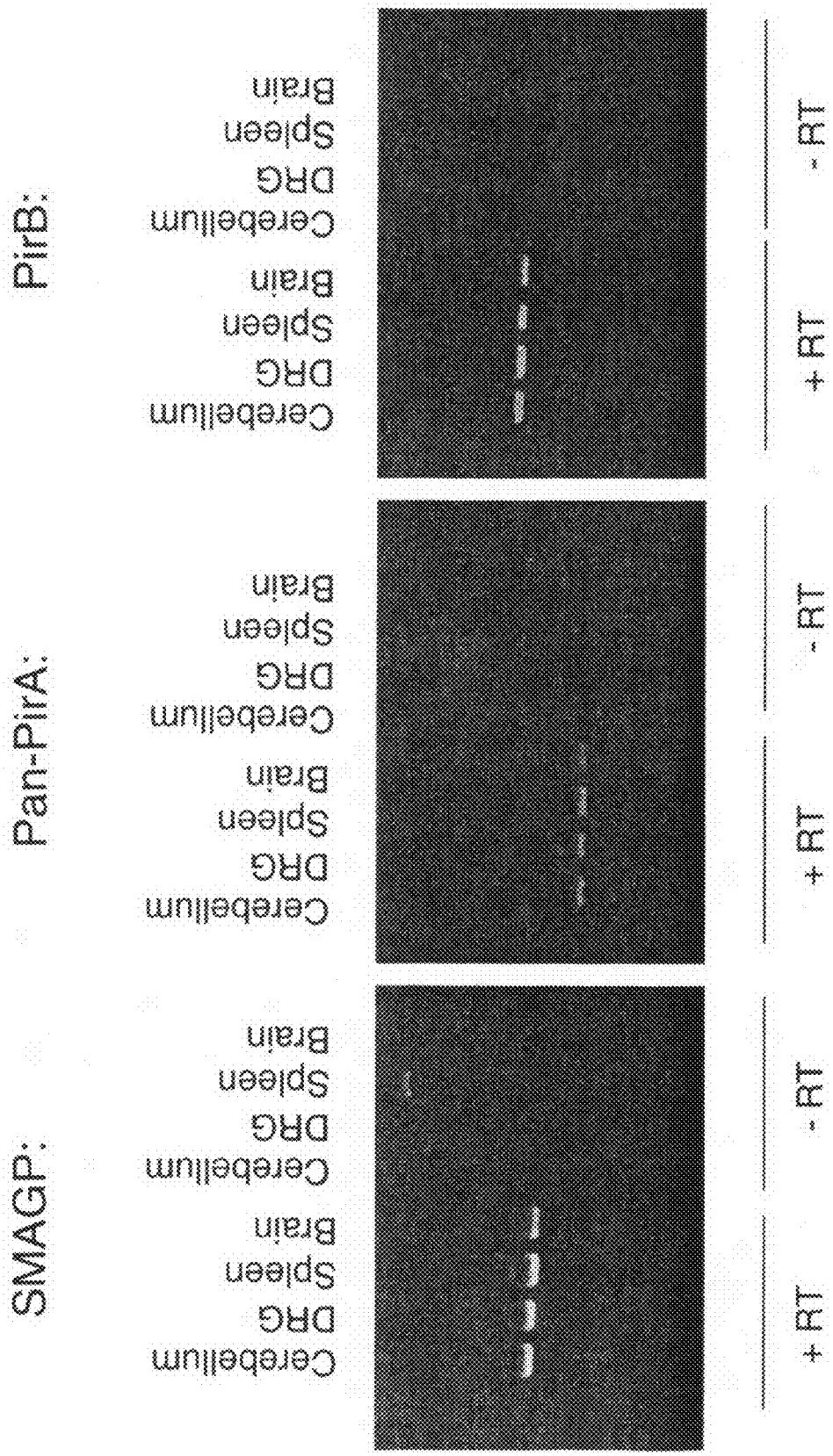
FIG. 3 shows RT-PCR results demonstrating the expression of SMAGP, PAN-PirA and PirB in various parts of the nervous system.

As shown in FIG. 3, RT-PCR analysis revealed that both PirB and PirA isoforms could be detected in cerebellum, DRG, and brain.

Example 5

In Situ Hybridization Results

To analyze the neuronal expression of PirB in greater detail, in situ hybridization analyses were performed. Adult or postnatal mice were perfused, and then brain and DRG were dissected out and post-fixed overnight. Tissues were subsequently cryo-protected in 30% sucrose, and embedded and frozen in O.C.T. Compound (Tissue-Tek). Frozen tissues were sectioned at 12 micron thickness. Radioactive probes were prepared using the MAXIscript in vitro transcription kit (Ambion), following manufacturer's protocols. In situ hybridization was carried out using the mRNA locator ISH kit (Ambion), according to the manufacturer's protocols.

The PirB probe was designed to hybridize to nucleotides #1922-2385, which are in the transmembrane and intracellular domain unique to PirB. Primers used to amplify this region were 5'TGAAGGCTCTCATTGGAGTGTCTG3' (SEQ ID NO: 8) and 5'GGCATAGGTCACATCCTGGGAC3' (SEQ ID NO: 9). The 464 bp fragment was cloned into pCRII-TOPO (Invitrogen).

Figure 4A:
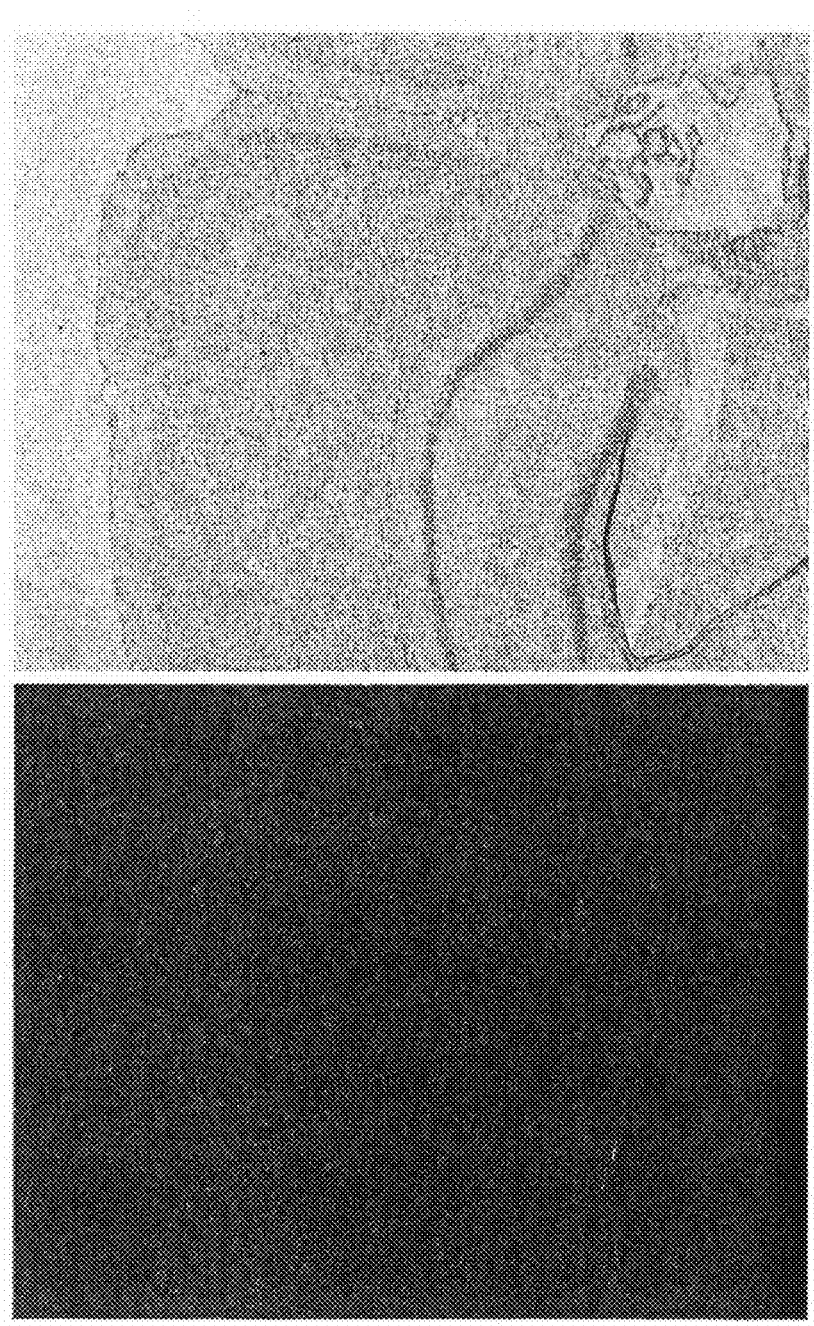
FIGS. 4A-4C confirm, by in situ hybridization, the expression of PirB in adult forebrain (A), adult cerebellum (B) and P10 Dorsal Root Ganglion (C).
Figure 4B:
Figure 4C:
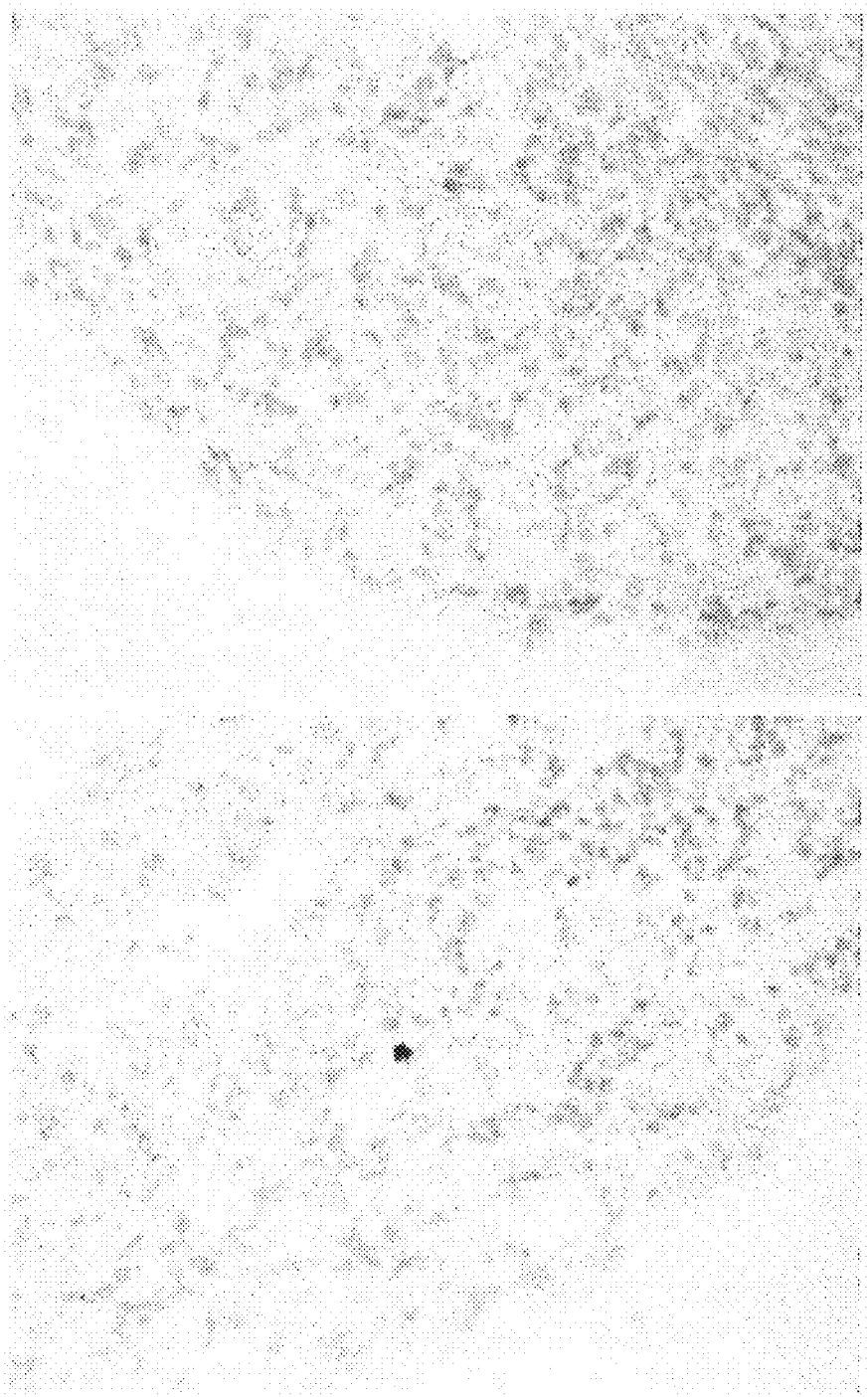

The results of in situ hybridization are shown in FIGS. 4A-4C. Positive hybridization signal is seen throughout the cortex, in the hippocampus, in the cerebellum, and in cells of the DRG.

Example 6

Nogo66 Inhibition of Axonal Growth and its Rescue by PirB ECD in Cerebellar Granule Neurons In this experiment, Nogo-66's ability to inhibit axonal growth was confirmed. Furthermore, PirB extracellular domain constructs were tested for their ability to interfere Nogo-66 inhibitory activity.

AP-Nogo66 was generated by cloning the 66 amino acid inhibitory loop of NogoA downstream of the human placental alkaline phosphatase (AP) gene. The construct was FLAG-tagged at the N-terminus to allow purification, and inserted into a pRK vector backbone (Genentech). To generate PirB extracellular domain (ECD) proteins amino acids #1-638 of PirB were cloned into pRK expression vectors upstream of either an 8-His tag (PirBHis) or human Fc (PirBFc). These expression constructs were transiently transfected into CHO cells, and the secreted proteins were purified from the conditioned medium by affinity chromatography.

Cerebellar granule neurons (CGN) were isolated from P7 CD1 mice, and cultured on immobilized AP-Nogo66 protein for inhibition assays. Briefly, 96 well plates pre-coated with poly-D-lysine (Biocoat, Becton Dickinson) were spotted with recombinant AP-Nogo66 (180 or 300 ng/3 ul spot). The AP-Nogo66 was coated alone, or mixed with an excess of either PirBFc (850 ng/3 ul spot) or PirBHis (1000 ng/3 ul spot). This resulted in spots containing a 2-4 fold molar excess of PirB ECD. Spotted proteins were allowed to adhere for 2 hours, and then plates were treated with 10 ug/ml laminin (Invitrogen) for 2 hr. Mouse P7 cerebellar cells were prepared as described (Zheng et al., 2005) and plated at a density of $2 \times 10^4$ cells/well. Cultures were incubated at 37° for 22 hrs, fixed with 4% paraformaldehyde/4% sucrose, and stained with an anti-tubulin antibody (TuJ1, Covance).

Images were captured with the ImageXpress imaging system (Molecular Devices).

Figure 6:
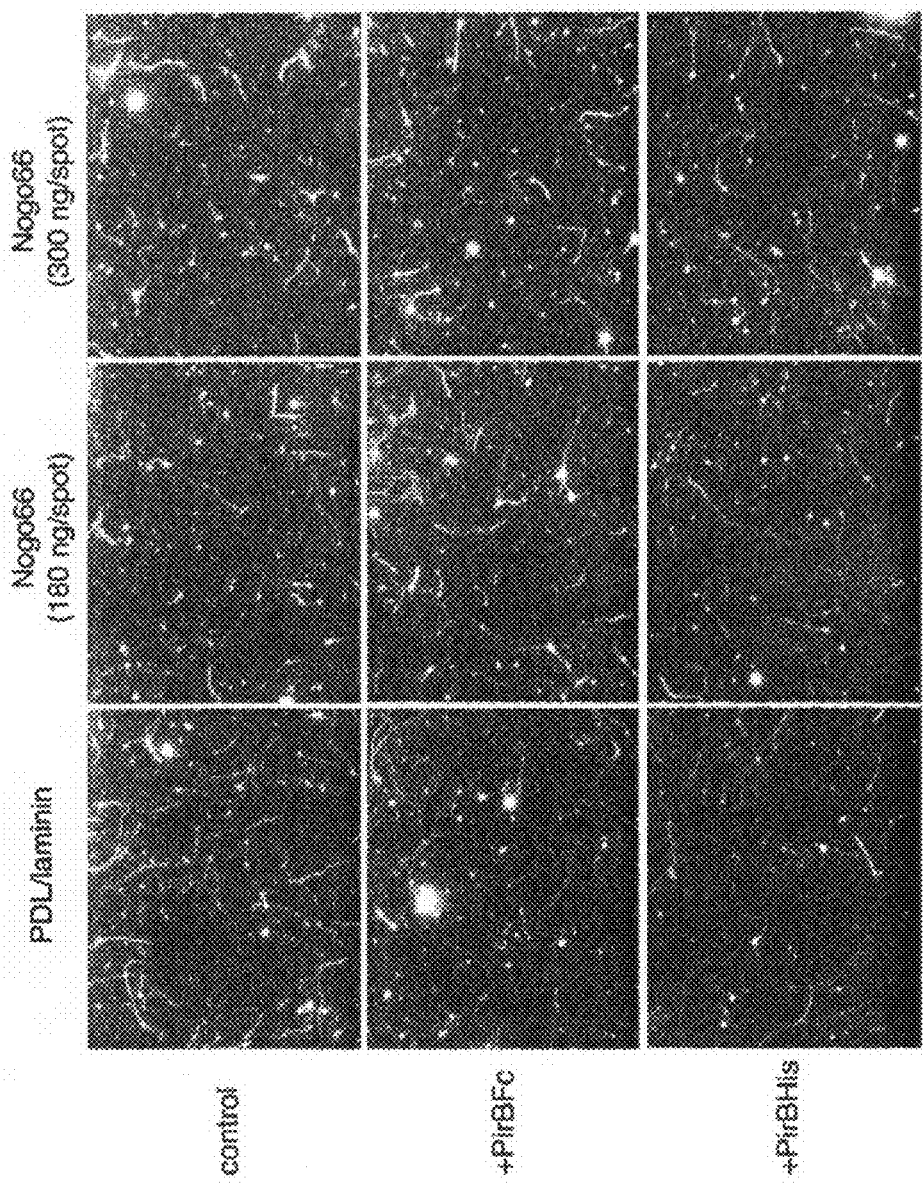
FIG. 6 illustrates Nogo66 inhibition of axonal growth, and reverse of such inhibition by PirB ECD (both PirBFc and PirBHis). Cerebellar granule neurons were used for the assay.

As shown in FIG. 6, AP-Nogo66 strongly inhibits axon outgrowth from P7 cerebellar neurons. The presence of an excess of PirB ECD, either with PirBFc or PirBHis, significantly reduced this inhibition. Inclusion of other control proteins (Fc or Robo4Fc) with AP-Nogo66 did not reduce inhibition.

Example 7

Co-Immunoprecipitation of PirB and NgR

This experiment explore the relationship and potential interaction of PirB and NgR when co-expressed in host cells in vitro.

COS7 cells were transiently transfected with a control vector, full-length PirB, or a mixture of full-length PirB and full-length NgR. 48 hours after transfection, cells were lysed with Cell Lysis Buffer (Cell Signaling Technology) and lysates were immunoprecipitated with anti-PirA/B (6C1, Pharmingen). Samples were separated by SDS-PAGE, transferred to nitrocellulose, and probed with anti-NgR (Alpha Diagnostics International).

Figure 7:
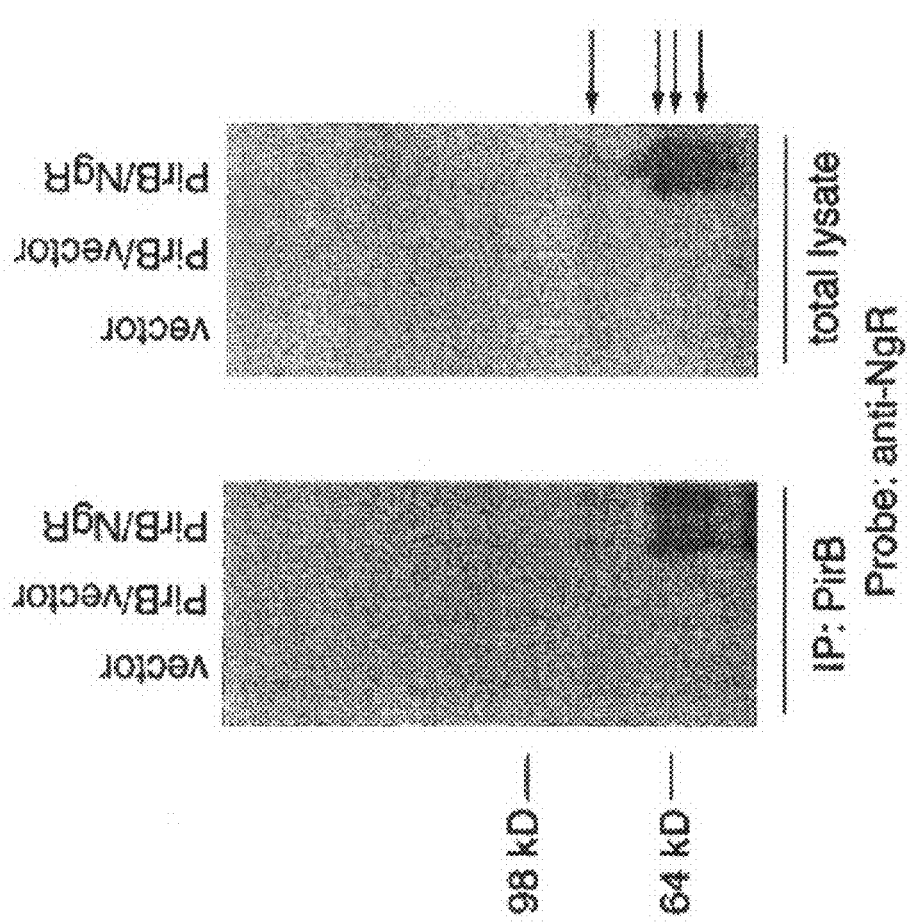
FIG. 7 shows co-immunoprecipitation of PirB and NgR. NgR is robustly co-precipitated with PirB (left panel). The right panel shows total protein from whole cell lysates immunoblotted with anti-NgR. The multiple bands (arrows) represent NgR processed by glycosylation to varying extents.

As shown in FIG. 7, NgR was robustly co-precipitated with PirB (left panel). The right panel shows total protein from whole cell lysates immunoblotted with anti-NgR. The multiple bands (arrows) represent NgR processed by glycosylation to varying extents.

Example 8

PirB Antibodies and Their Use to Interfere with Nogo66 Axonal Growth Inhibitory Activity In this experiment, antibodies against PirB were tested for their ability to interfere with Nogo-66 induced inhibition of axonal growth.

Figure 8:
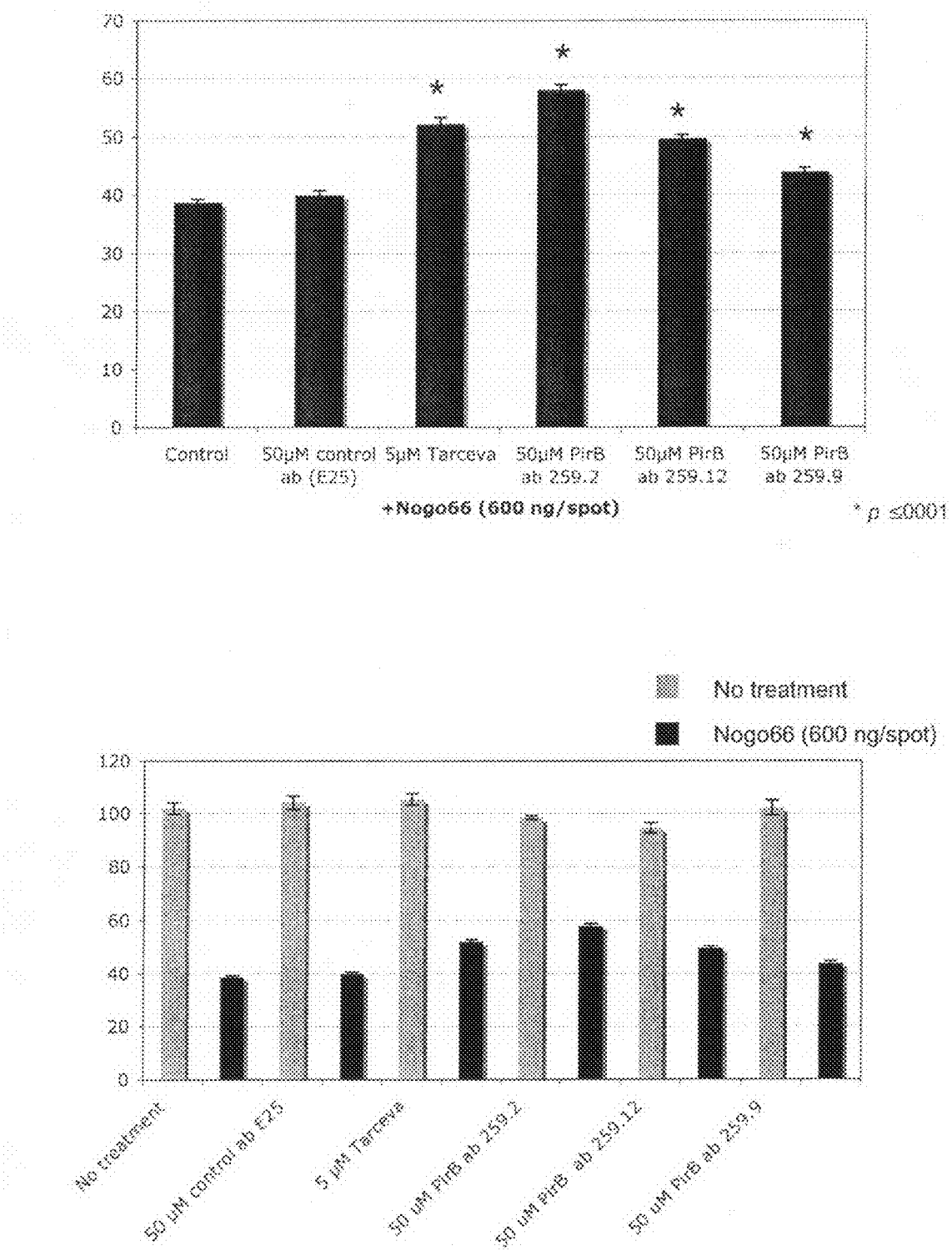
FIG. 8 shows that Nogo66 inhibition of axonal growth is partially rescued by anti-PirB antibodies in cerebellar granule neurons.

Cerebellar granule neurons (CGN) were isolated from P7 CD1 mice and cultured on immobilized AP-Nogo66 protein for inhibition assays, as described in the previous examples. Function-blocking antibodies were generated by screening PirB ECD against a human synthetic antibody phage library, essentially as described in Liang et al., *J. Mol. Biol.* 366(3): 815-819 (2006), which is incorporated by reference herein in its entirety. Clones were selected for their ability to compete with AP-Nogo66 binding to PirB. In this experiment, anti-PirB or control antibodies were incubated with neurons grown on AP-Nogo66. As shown in FIG. 8, the anti-PirB antibodies led to a significant decreased in inhibition by AP-Nogo66.

All references cited throughout the disclosure are hereby expressly incorporated by reference in their entirety.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

What is claimed is:

1. A method for identifying a paired-immunoglobulin-like receptor B/leukocyte immunoglobulin-like receptor, subfamily B (PirB/LILRB) antagonist comprising the steps of:
   a) contacting a candidate agent with a complex comprising PirB/LILRB and myelin or a myelin-associated protein, or a fragment of myelin, MAG, Nogo or OMgp;
   b) detecting the ability of said candidate agent to inhibit the binding between PirB/LILRB and said myelin or myelin-associated protein, or said fragment, wherein said PirB/LILRB is selected from the group consisting of LILRB1, LILRB2, LILRB3, and LILRB5; and
   c) selecting a candidate agent that inhibits said binding, wherein said candidate agent is identified as a PirB/LILRB antagonist if the binding is inhibited.

2. The method of claim 1, wherein step b) of the method further comprises measuring inhibition of cellular signaling.

3. The method of claim 2 wherein said cellular signaling results in the inhibition of axonal outgrowth or neuronal regeneration.

4. The method of claim 1 wherein the myelin-associated protein is selected from the group consisting of Nogo, MAG and OMgp.

5. The method of claim 1 wherein said PirB/LILRB is selected from the group consisting of LILRB2, transcript variant 1 (SEQ ID NO: 2); LILRB2, transcript variant 2 (SEQ ID NO: 14); LILRB1, transcript variant 1 (SEQ ID NO: 10); LILRB1, transcript variant 2 (SEQ ID NO: 11); LILRB1, transcript variant 3 (SEQ ID NO: 12); LILRB1, transcript variant 4 (SEQ ID NO: 13); LILRB3, transcript variant 1 (SEQ ID NO: 15); LILRB3, transcript variant 2 (SEQ ID NO: 16); LILRB5, transcript variant 1 (SEQ ID NO: 17); LILRB5, transcript variant 2 (SEQ ID NO: 18); and LILRB5, transcript variant 3 (SEQ ID NO: 19).

6. The method of claim 5 wherein said PirB is LILRB3, transcript variant 1 (SEQ ID NO: 15); LILRB2, transcript variant 1 (SEQ ID NO: 2); or LILRB2, transcript variant 2 (SEQ ID NO: 14).

7. The method of claim 4 wherein the complex further comprises NgR.

8. The method of claim 1 wherein the candidate agent is selected from the group consisting of antibodies, polypeptides, peptides, nucleic acids, short interfering RNAs (siRNAs), small organic molecules, polysaccharides and polynucleotides.

9. The method of claim 8 wherein the candidate agent is an antibody.

10. The method of claim 9 wherein said antibody specifically binds said PirB/LILRB.

11. The method of claim 10 wherein said antibody specifically binds an LILRB2 or LILRB3.

12. The method of claim 10 wherein said antibody is a monoclonal antibody.

13. The method of claim 10 wherein said antibody is a chimeric antibody.

14. The method of claim 10 wherein said antibody is a humanized antibody.

15. The method of claim 10 wherein said antibody is a human antibody.

16. The method of claim 10 wherein said antibody is an antigen-binding fragment.

17. The method of claim 16 wherein said antibody fragment is selected from the group consisting of Fv, Fab, Fab', and F(ab')$_2$ fragments.

18. The method of claim 8 wherein the candidate agent is a short-interfering RNA (siRNA).

19. The method of claim 1 wherein at least one of said PirB/LILRB and said myelin or myelin-associated protein, or said fragment, is immobilized.

20. The method of claim 1 which is a cell-based assay.

21. The method of claim 20 wherein said cell-based assay comprises culturing neuronal cells with said myelin or myelin-associated protein, or fragment thereof, in the presence and absence of said candidate agent and determining a change in neurite length, wherein said candidate agent is identified as an antagonist when the neurite length is longer in the presence of said candidate agent.

22. The method of claim 21 wherein said neuronal cells are primary neurons.

23. The method of claim 21 wherein said neuronal cells are derived from embryonic stem (ES) cells or cell lines.

24. The method of claim 23 wherein said neuronal cells are derived from neuroblastoma.

25. The method of claim 21 wherein said neuronal cells are selected from the group consisting of cerebellar granule neurons, dorsal root ganglion neurons, and cortical neurons.

* * * * *

SEQUENCE LISTING

<160> NUMBER OF SEQ ID NOS: 20

<210> SEQ ID NO 1
<211> LENGTH: 841

```
<212> TYPE: PRT
<213> ORGANISM: Mus Musculus

<400> SEQUENCE: 1

Met Ser Cys Thr Phe Thr Ala Leu Leu Arg Leu Gly Leu Thr Leu Ser
 1               5                  10                  15

Leu Trp Ile Pro Val Leu Thr Gly Ser Leu Pro Lys Pro Ile Leu Arg
             20                  25                  30

Val Gln Pro Asp Ser Val Val Ser Arg Trp Thr Lys Val Thr Phe Phe
         35                  40                  45

Cys Glu Glu Thr Ile Gly Ala Asn Glu Tyr Arg Leu Tyr Lys Asp Gly
 50                  55                  60

Lys Leu Tyr Lys Thr Val Thr Lys Asn Lys Gln Lys Pro Ala Asn Lys
 65                  70                  75                  80

Ala Glu Phe Ser Leu Ser Asn Val Asp Leu Arg Asn Ala Gly Gln Tyr
                 85                  90                  95

Arg Cys Ser Tyr Ser Thr Gln Tyr Lys Ser Ser Gly Tyr Ser Asp Pro
            100                 105                 110

Leu Glu Leu Val Val Thr Gly Asp Tyr Trp Thr Pro Ser Leu Leu Ala
        115                 120                 125

Gln Ala Ser Pro Val Val Thr Ser Gly Gly Tyr Val Thr Leu Gln Cys
    130                 135                 140

Glu Ser Trp His Asn Asp His Lys Phe Ile Leu Thr Val Glu Gly Pro
145                 150                 155                 160

Gln Lys Leu Ser Trp Thr Gln Asp Ser Gln Tyr Asn Tyr Ser Thr Arg
                165                 170                 175

Lys Tyr His Ala Leu Phe Ser Val Gly Pro Val Thr Pro Asn Gln Arg
            180                 185                 190

Trp Ile Cys Arg Cys Tyr Ser Tyr Asp Arg Asn Arg Pro Tyr Val Trp
        195                 200                 205

Ser Pro Pro Ser Glu Ser Val Glu Leu Leu Val Ser Gly Asn Leu Gln
    210                 215                 220

Lys Pro Thr Ile Lys Ala Glu Pro Gly Pro Val Ile Ala Ser Lys Arg
225                 230                 235                 240

Ala Met Thr Ile Trp Cys Gln Gly Asn Leu Asp Ala Glu Val Tyr Phe
                245                 250                 255

Leu His Asn Glu Gly Ser Gln Lys Thr Gln Ser Thr Gln Thr Leu Gln
            260                 265                 270

Gln Pro Gly Asn Lys Gly Lys Phe Phe Ile Pro Ser Met Thr Arg Gln
        275                 280                 285

His Ala Gly Gln Tyr Arg Cys Tyr Cys Tyr Gly Ser Ala Gly Trp Ser
    290                 295                 300

Gln Pro Ser Asp Thr Leu Glu Leu Val Val Thr Gly Ile Tyr Glu His
305                 310                 315                 320

Tyr Lys Pro Arg Leu Ser Val Leu Pro Ser Pro Val Val Thr Ala Gly
                325                 330                 335

Gly Asn Met Thr Leu His Cys Ala Ser Asp Phe His Tyr Asp Lys Phe
            340                 345                 350

Ile Leu Thr Lys Glu Asp Lys Lys Phe Gly Asn Ser Leu Asp Thr Glu
        355                 360                 365

His Ile Ser Ser Ser Arg Gln Tyr Arg Ala Leu Phe Ile Ile Gly Pro
    370                 375                 380

Thr Thr Pro Thr His Thr Gly Thr Phe Arg Cys Tyr Gly Tyr Phe Lys
385                 390                 395                 400
```

```
Asn Ala Pro Gln Leu Trp Ser Val Pro Ser Asp Leu Gln Gln Ile Leu
                405                 410                 415
Ile Ser Gly Leu Ser Lys Lys Pro Ser Leu Leu Thr His Gln Gly His
            420                 425                 430
Ile Leu Asp Pro Gly Met Thr Leu Thr Leu Gln Cys Tyr Ser Asp Ile
        435                 440                 445
Asn Tyr Asp Arg Phe Ala Leu His Lys Val Gly Gly Ala Asp Ile Met
450                 455                 460
Gln His Ser Ser Gln Gln Thr Asp Thr Gly Phe Ser Val Ala Asn Phe
465                 470                 475                 480
Thr Leu Gly Tyr Val Ser Ser Ser Thr Gly Gln Tyr Arg Cys Tyr
                485                 490                 495
Gly Ala His Asn Leu Ser Ser Glu Trp Ser Ala Ser Ser Glu Pro Leu
                500                 505                 510
Asp Ile Leu Ile Thr Gly Gln Leu Pro Leu Thr Pro Ser Leu Ser Val
            515                 520                 525
Lys Pro Asn His Thr Val His Ser Gly Glu Thr Val Ser Leu Leu Cys
        530                 535                 540
Trp Ser Met Asp Ser Val Asp Thr Phe Ile Leu Ser Lys Glu Gly Ser
545                 550                 555                 560
Ala Gln Gln Pro Leu Arg Leu Lys Ser Lys Ser His Asp Gln Gln Ser
                565                 570                 575
Gln Ala Glu Phe Ser Met Ser Ala Val Thr Ser His Leu Ser Gly Thr
                580                 585                 590
Tyr Arg Cys Tyr Gly Ala Gln Asn Ser Ser Phe Tyr Leu Leu Ser Ser
            595                 600                 605
Ala Ser Ala Pro Val Glu Leu Thr Val Ser Gly Pro Ile Glu Thr Ser
        610                 615                 620
Thr Pro Pro Pro Thr Met Ser Met Pro Leu Gly Gly Leu His Met Tyr
625                 630                 635                 640
Leu Lys Ala Leu Ile Gly Val Ser Val Ala Phe Ile Leu Phe Leu Phe
                645                 650                 655
Ile Leu Ile Phe Ile Leu Leu Arg Arg Arg His Arg Gly Lys Phe Arg
                660                 665                 670
Lys Asp Val Gln Lys Glu Lys Asp Leu Gln Leu Ser Ser Gly Ala Glu
            675                 680                 685
Glu Pro Ile Thr Arg Lys Gly Glu Leu Gln Lys Arg Pro Asn Pro Ala
        690                 695                 700
Ala Ala Thr Gln Glu Glu Ser Leu Tyr Ala Ser Val Glu Asp Met Gln
705                 710                 715                 720
Thr Glu Asp Gly Val Glu Leu Asn Ser Trp Thr Pro Glu Glu Asp
                725                 730                 735
Pro Gln Gly Glu Thr Tyr Ala Gln Val Lys Pro Ser Arg Leu Arg Lys
                740                 745                 750
Ala Gly His Val Ser Pro Ser Val Met Ser Arg Glu Gln Leu Asn Thr
            755                 760                 765
Glu Tyr Glu Gln Ala Glu Gly Gln Gly Ala Asn Asn Gln Ala Ala
        770                 775                 780
Glu Ser Gly Glu Ser Gln Asp Val Thr Tyr Ala Gln Leu Cys Ser Arg
785                 790                 795                 800
Thr Leu Arg Gln Gly Ala Ala Ala Ser Pro Leu Ser Gln Ala Gly Glu
                805                 810                 815
Ala Pro Glu Glu Pro Ser Val Tyr Ala Thr Leu Ala Ala Ala Arg Pro
            820                 825                 830
```

Glu Ala Val Pro Lys Asp Val Glu Gln
        835                 840

<210> SEQ ID NO 2
<211> LENGTH: 598
<212> TYPE: PRT
<213> ORGANISM: Homo Sapiens

<400> SEQUENCE: 2

Met Thr Pro Ile Val Thr Val Leu Ile Cys Leu Gly Leu Ser Leu Gly
  1               5                  10                  15

Pro Arg Thr His Val Gln Thr Gly Thr Ile Pro Lys Pro Thr Leu Trp
                 20                  25                  30

Ala Glu Pro Asp Ser Val Ile Thr Gln Gly Ser Pro Val Thr Leu Ser
             35                  40                  45

Cys Gln Gly Ser Leu Glu Ala Gln Glu Tyr Arg Leu Tyr Arg Glu Lys
         50                  55                  60

Lys Ser Ala Ser Trp Ile Thr Arg Ile Arg Pro Glu Leu Val Lys Asn
 65                  70                  75                  80

Gly Gln Phe His Ile Pro Ser Ile Thr Trp Glu His Thr Gly Arg Tyr
                 85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
        130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala Tyr Asn Leu Ser Ser
    290                 295                 300

Glu Trp Ser Ala Pro Ser Asp Pro Leu Asp Ile Leu Ile Thr Gly Gln
305                 310                 315                 320

Ile His Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

-continued

Arg Ser Ile His Glu Tyr Pro Lys Tyr Gln Ala Glu Phe Pro Met Ser
        370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
            435                 440                 445

Ser Asp Pro Gln Ser Gly Leu Gly Arg His Leu Gly Val Val Ile Gly
        450                 455                 460

Ile Leu Val Ala Val Leu Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys Asp Thr Gln Pro Glu Asp Gly
530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
            580                 585                 590

Ala Thr Leu Ala Ile His
        595

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggcataggtc acatcctggg ac                                    22

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gtctcagaaa ccattgaatc c                                     21

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gacagaaaac tttgggtcat cag                                          23

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ccctcagcaa cgatgaacaa cc                                           22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
tggaccctgg agtcagtgat tc                                           22

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
tgaaggctct cattggagtg tctg                                         24

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ggcataggtc acatcctggg ac                                           22

<210> SEQ ID NO 10
<211> LENGTH: 650
<212> TYPE: PRT
<213> ORGANISM: Homo Sapiens

<400> SEQUENCE: 10

```
Met Thr Pro Ile Leu Thr Val Leu Ile Cys Leu Gly Leu Ser Leu Gly
 1               5                  10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
```

```
            115                 120                 125
Ala Gln Pro Ser Pro Val Val Asn Ser Gly Gly Asn Val Ile Leu Gln
            130                 135                 140
Cys Asp Ser Gln Val Ala Phe Asp Gly Phe Ser Leu Cys Lys Glu Gly
145                 150                 155                 160
Glu Asp Glu His Pro Gln Cys Leu Asn Ser Gln Pro His Ala Arg Gly
            165                 170                 175
Ser Ser Arg Ala Ile Phe Ser Val Gly Pro Val Ser Pro Arg Arg
            180                 185                 190
Trp Trp Tyr Arg Cys Tyr Ala Tyr Asp Ser Asn Ser Pro Tyr Glu Trp
            195                 200                 205
Ser Leu Pro Ser Asp Leu Leu Glu Leu Leu Val Leu Gly Val Ser Lys
            210                 215                 220
Lys Pro Ser Leu Ser Val Gln Pro Gly Pro Ile Val Ala Pro Glu Glu
225                 230                 235                 240
Thr Leu Thr Leu Gln Cys Gly Ser Asp Ala Gly Tyr Asn Arg Phe Val
            245                 250                 255
Leu Tyr Lys Asp Gly Glu Arg Asp Phe Leu Gln Leu Ala Gly Ala Gln
            260                 265                 270
Pro Gln Ala Gly Leu Ser Gln Ala Asn Phe Thr Leu Gly Pro Val Ser
            275                 280                 285
Arg Ser Tyr Gly Gly Gln Tyr Arg Cys Tyr Gly Ala His Asn Leu Ser
            290                 295                 300
Ser Glu Trp Ser Ala Pro Ser Asp Pro Leu Asp Ile Leu Ile Ala Gly
305                 310                 315                 320
Gln Phe Tyr Asp Arg Val Ser Leu Ser Val Gln Pro Gly Pro Thr Val
            325                 330                 335
Ala Ser Gly Glu Asn Val Thr Leu Leu Cys Gln Ser Gln Gly Trp Met
            340                 345                 350
Gln Thr Phe Leu Leu Thr Lys Glu Gly Ala Ala Asp Asp Pro Trp Arg
            355                 360                 365
Leu Arg Ser Thr Tyr Gln Ser Gln Lys Tyr Gln Ala Glu Phe Pro Met
            370                 375                 380
Gly Pro Val Thr Ser Ala His Ala Gly Thr Tyr Arg Cys Tyr Gly Ser
385                 390                 395                 400
Gln Ser Ser Lys Pro Tyr Leu Leu Thr His Pro Ser Asp Pro Leu Glu
            405                 410                 415
Leu Val Val Ser Gly Pro Ser Gly Gly Pro Ser Ser Pro Thr Thr Gly
            420                 425                 430
Pro Thr Ser Thr Ser Gly Pro Glu Asp Gln Pro Leu Thr Pro Thr Gly
            435                 440                 445
Ser Asp Pro Gln Ser Gly Leu Gly Arg His Leu Gly Val Val Ile Gly
            450                 455                 460
Ile Leu Val Ala Val Ile Leu Leu Leu Leu Leu Leu Leu Leu Leu Phe
465                 470                 475                 480
Leu Ile Leu Arg His Arg Arg Gln Gly Lys His Trp Thr Ser Thr Gln
            485                 490                 495
Arg Lys Ala Asp Phe Gln His Pro Ala Gly Ala Val Gly Pro Glu Pro
            500                 505                 510
Thr Asp Arg Gly Leu Gln Trp Arg Ser Ser Pro Ala Ala Asp Ala Gln
            515                 520                 525
Glu Glu Asn Leu Tyr Ala Ala Val Lys His Thr Gln Pro Glu Asp Gly
            530                 535                 540
```

```
Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ser Glu Ala
        595                 600                 605

Pro Gln Asp Val Thr Tyr Ala Gln Leu His Ser Leu Thr Leu Arg Arg
        610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
            645                 650

<210> SEQ ID NO 11
<211> LENGTH: 652
<212> TYPE: PRT
<213> ORGANISM: Homo Sapiens

<400> SEQUENCE: 11

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
                100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
                180                 185                 190

Trp Trp Tyr Arg Cys Tyr Ala Tyr Asp Ser Asn Ser Pro Tyr Glu Trp
            195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270
```

-continued

```
Pro Gln Ala Gly Leu Ser Gln Ala Asn Phe Thr Leu Gly Pro Val Ser
    275                 280                 285

Arg Ser Tyr Gly Gly Gln Tyr Arg Cys Tyr Gly Ala His Asn Leu Ser
290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
                340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
        370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
                420                 425                 430

Pro Thr Ser Thr Ser Ala Gly Pro Glu Asp Gln Pro Leu Thr Pro Thr
            435                 440                 445

Gly Ser Asp Pro Gln Ser Gly Leu Gly Arg His Leu Gly Val Val Ile
        450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
                500                 505                 510

Pro Thr Asp Arg Gly Leu Gln Trp Arg Ser Ser Pro Ala Ala Asp Ala
            515                 520                 525

Gln Glu Glu Asn Leu Tyr Ala Ala Val Lys His Thr Gln Pro Glu Asp
        530                 535                 540

Gly Val Glu Met Asp Thr Arg Gln Ser Pro His Asp Glu Asp Pro Gln
545                 550                 555                 560

Ala Val Thr Tyr Ala Glu Val Lys His Ser Arg Pro Arg Arg Glu Met
                565                 570                 575

Ala Ser Pro Pro Ser Pro Leu Ser Gly Glu Phe Leu Asp Thr Lys Asp
                580                 585                 590

Arg Gln Ala Glu Glu Asp Arg Gln Met Asp Thr Glu Ala Ala Ala Ser
            595                 600                 605

Glu Ala Pro Gln Asp Val Thr Tyr Ala Gln Leu His Ser Leu Thr Leu
        610                 615                 620

Arg Arg Glu Ala Thr Glu Pro Pro Pro Ser Gln Glu Gly Pro Ser Pro
625                 630                 635                 640

Ala Val Pro Ser Ile Tyr Ala Thr Leu Ala Ile His
                645                 650
```

<210> SEQ ID NO 12
<211> LENGTH: 651
<212> TYPE: PRT
<213> ORGANISM: Homo Sapiens

<400> SEQUENCE: 12

-continued

```
Met Thr Pro Ile Leu Thr Val Leu Ile Cys Leu Gly Leu Ser Leu Gly
 1               5                  10                  15

Pro Arg Thr His Val Gln Ala Gly His Leu Pro Lys Pro Thr Leu Trp
                 20                  25                  30

Ala Glu Pro Gly Ser Val Ile Thr Gln Gly Ser Pro Val Thr Leu Arg
             35                  40                  45

Cys Gln Gly Gly Gln Glu Thr Gln Glu Tyr Arg Leu Tyr Arg Glu Lys
 50                  55                  60

Lys Thr Ala Leu Trp Ile Thr Arg Ile Pro Gln Glu Leu Val Lys Lys
 65                  70                  75                  80

Gly Gln Phe Pro Ile Pro Ser Ile Thr Trp Glu His Ala Gly Arg Tyr
                 85                  90                  95

Arg Cys Tyr Tyr Gly Ser Asp Thr Ala Gly Arg Ser Glu Ser Ser Asp
             100                 105                 110

Pro Leu Glu Leu Val Val Thr Gly Ala Tyr Ile Lys Pro Thr Leu Ser
         115                 120                 125

Ala Gln Pro Ser Pro Val Val Asn Ser Gly Gly Asn Val Ile Leu Gln
     130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                 165                 170                 175

Ser Ser Arg Ala Ile Phe Ser Val Gly Pro Val Ser Pro Ser Arg Arg
             180                 185                 190

Trp Trp Tyr Arg Cys Tyr Ala Tyr Asp Ser Asn Ser Pro Tyr Glu Trp
         195                 200                 205

Ser Leu Pro Ser Asp Leu Leu Glu Leu Leu Val Leu Gly Val Ser Lys
     210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                 245                 250                 255

Leu Tyr Lys Asp Gly Glu Arg Asp Phe Leu Gln Leu Ala Gly Ala Gln
             260                 265                 270

Pro Gln Ala Gly Leu Ser Gln Ala Asn Phe Thr Leu Gly Pro Val Ser
         275                 280                 285

Arg Ser Tyr Gly Gly Gln Tyr Arg Cys Tyr Gly Ala His Asn Leu Ser
     290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                 325                 330                 335

Ala Ser Gly Glu Asn Val Thr Leu Leu Cys Gln Ser Gln Gly Trp Met
             340                 345                 350

Gln Thr Phe Leu Leu Thr Lys Glu Gly Ala Ala Asp Asp Pro Trp Arg
         355                 360                 365

Leu Arg Ser Thr Tyr Gln Ser Gln Lys Tyr Gln Ala Glu Phe Pro Met
     370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                 405                 410                 415

Leu Val Val Ser Gly Pro Ser Gly Pro Ser Ser Pro Thr Thr Gly
             420                 425                 430
```

```
Pro Thr Ser Thr Ser Ala Gly Pro Glu Asp Gln Pro Leu Thr Pro Thr
            435                 440                 445

Gly Ser Asp Pro Gln Ser Gly Leu Gly Arg His Leu Gly Val Val Ile
        450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
            500                 505                 510

Pro Thr Asp Arg Gly Leu Gln Trp Arg Ser Pro Ala Ala Asp Ala
        515                 520                 525

Gln Glu Glu Asn Leu Tyr Ala Ala Val Lys His Thr Gln Pro Glu Asp
            530                 535                 540

Gly Val Glu Met Asp Thr Arg Ser Pro His Asp Glu Asp Pro Gln Ala
545                 550                 555                 560

Val Thr Tyr Ala Glu Val Lys His Ser Arg Pro Arg Arg Glu Met Ala
                565                 570                 575

Ser Pro Pro Ser Pro Leu Ser Gly Glu Phe Leu Asp Thr Lys Asp Arg
            580                 585                 590

Gln Ala Glu Glu Asp Arg Gln Met Asp Thr Glu Ala Ala Ala Ser Glu
        595                 600                 605

Ala Pro Gln Asp Val Thr Tyr Ala Gln Leu His Ser Leu Thr Leu Arg
            610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 13
<211> LENGTH: 651
<212> TYPE: PRT
<213> ORGANISM: Homo Sapiens

<400> SEQUENCE: 13

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160
```

Glu Asp Glu His Pro Gln Cys Leu Asn Ser Gln Pro His Ala Arg Gly
            165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
            195                 200                 205

Ser Leu Pro Ser Asp Leu Leu Glu Leu Leu Val Leu Gly Val Ser Lys
            210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
            245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
            290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
            325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
            405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
            450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
            485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys His Thr Gln Pro Glu Asp Gly
            530                 535                 540

Val Glu Met Asp Thr Arg Gln Ser Pro His Asp Glu Asp Pro Gln Ala
545                 550                 555                 560

Val Thr Tyr Ala Glu Val Lys His Ser Arg Pro Arg Arg Glu Met Ala
            565                 570                 575

Ser Pro Pro Ser Pro Leu Ser Gly Glu Phe Leu Asp Thr Lys Asp Arg

```
                    580                 585                 590
Gln Ala Glu Glu Asp Arg Gln Met Asp Thr Glu Ala Ala Ser Glu
                595                 600                 605

Ala Pro Gln Asp Val Thr Tyr Ala Gln Leu His Ser Leu Thr Leu Arg
610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 14
<211> LENGTH: 597
<212> TYPE: PRT
<213> ORGANISM: Homo Sapiens

<400> SEQUENCE: 14

Met Thr Pro Ile Val Thr Val Leu Ile Cys Leu Gly Leu Ser Leu Gly
  1               5                  10                  15

Pro Arg Thr His Val Gln Thr Gly Thr Ile Pro Lys Pro Thr Leu Trp
                 20                  25                  30

Ala Glu Pro Asp Ser Val Ile Thr Gln Gly Ser Pro Val Thr Leu Ser
             35                  40                  45

Cys Gln Gly Ser Leu Glu Ala Gln Glu Tyr Arg Leu Tyr Arg Glu Lys
         50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                 85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
```

```
                305                 310                 315                 320
Ile Arg Gly Thr Pro Phe Ile Ser Val Gln Pro Gly Pro Thr Val Ala
                    325                 330                 335
Ser Gly Glu Asn Val Thr Leu Leu Cys Gln Ser Trp Arg Gln Phe His
                340                 345                 350
Thr Phe Leu Leu Thr Lys Ala Gly Ala Ala Asp Ala Pro Leu Arg Leu
            355                 360                 365
Arg Ser Ile His Glu Tyr Pro Lys Tyr Gln Ala Glu Phe Pro Met Ser
        370                 375                 380
Pro Val Thr Ser Ala His Ala Gly Thr Tyr Arg Cys Tyr Gly Ser Leu
385                 390                 395                 400
Asn Ser Asp Pro Tyr Leu Leu Ser His Pro Ser Glu Pro Leu Glu Leu
                405                 410                 415
Val Val Ser Gly Pro Ser Met Gly Ser Ser Pro Pro Thr Gly Pro
                    420                 425                 430
Ile Ser Thr Pro Gly Pro Glu Asp Gln Pro Leu Thr Pro Thr Gly Ser
                435                 440                 445
Asp Pro Gln Ser Gly Leu Gly Arg His Leu Gly Val Val Ile Gly Ile
            450                 455                 460
Leu Val Ala Val Val Leu Leu Leu Leu Leu Leu Leu Leu Phe Leu
465                 470                 475                 480
Ile Leu Arg His Arg Arg Gln Gly Lys His Trp Thr Ser Thr Gln Arg
                485                 490                 495
Lys Ala Asp Phe Gln His Pro Ala Gly Ala Val Gly Pro Glu Pro Thr
            500                 505                 510
Asp Arg Gly Leu Gln Trp Arg Ser Ser Pro Ala Ala Asp Ala Gln Glu
        515                 520                 525
Glu Asn Leu Tyr Ala Ala Val Lys Asp Thr Gln Pro Glu Asp Gly Val
        530                 535                 540
Glu Met Asp Thr Arg Ala Ala Ser Glu Ala Pro Gln Asp Val Thr
545                 550                 555                 560
Tyr Ala Gln Leu His Ser Leu Thr Leu Arg Arg Lys Ala Thr Glu Pro
                565                 570                 575
Pro Pro Ser Gln Glu Arg Glu Pro Pro Ala Glu Pro Ser Ile Tyr Ala
                580                 585                 590
Thr Leu Ala Ile His
        595

<210> SEQ ID NO 15
<211> LENGTH: 632
<212> TYPE: PRT
<213> ORGANISM: Homo Sapiens

<400> SEQUENCE: 15

Met Thr Pro Ala Leu Thr Ala Leu Leu Cys Leu Gly Leu Ser Leu Gly
1               5                   10                  15
Pro Arg Thr Arg Val Gln Ala Gly Pro Phe Pro Lys Pro Thr Leu Trp
            20                  25                  30
Ala Glu Pro Gly Ser Val Ile Ser Trp Gly Ser Pro Val Thr Ile Trp
        35                  40                  45
Cys Gln Gly Ser Gln Glu Ala Gln Glu Tyr Arg Leu His Lys Glu Gly
    50                  55                  60
Ser Pro Glu Pro Leu Asp Arg Asn Asn Pro Leu Glu Pro Lys Asn Lys
65                  70                  75                  80
Ala Arg Phe Ser Ile Pro Ser Met Thr Glu His His Ala Gly Arg Tyr
```

-continued

```
                85                  90                  95
Arg Cys His Tyr Tyr Ser Ser Ala Gly Trp Ser Glu Pro Ser Asp Pro
                    100                 105                 110

Leu Glu Met Val Met Thr Gly Ala Tyr Ser Lys Pro Thr Leu Ser Ala
            115                 120                 125

Leu Pro Ser Pro Val Val Ala Ser Gly Gly Asn Met Thr Leu Arg Cys
        130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Arg Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Thr Asn Thr Pro Trp Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asn Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser Asn Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser His Pro Ser Glu Pro Leu Glu Leu
                405                 410                 415

Val Val Ser Gly His Ser Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe Leu Leu Leu
    450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510
```

-continued

```
Leu Tyr Ala Ala Val Lys Asp Thr Gln Ser Glu Asp Arg Val Glu Leu
            515                 520                 525

Asp Ser Gln Gln Ser Pro His Asp Glu Asp Pro Gln Ala Val Thr Tyr
    530                 535                 540

Ala Pro Val Lys His Ser Ser Pro Arg Arg Glu Met Ala Ser Pro Pro
545                 550                 555                 560

Ser Ser Leu Ser Gly Glu Phe Leu Asp Thr Lys Asp Arg Gln Val Glu
                565                 570                 575

Glu Asp Arg Gln Met Asp Thr Glu Ala Ala Ser Glu Ala Ser Gln
            580                 585                 590

Asp Val Thr Tyr Ala Gln Leu His Ser Leu Thr Leu Arg Arg Lys Ala
                595                 600                 605

Thr Glu Pro Pro Pro Ser Gln Glu Gly Glu Pro Pro Ala Glu Pro Ser
610                 615                 620

Ile Tyr Ala Thr Leu Ala Ile His
625                 630

<210> SEQ ID NO 16
<211> LENGTH: 631
<212> TYPE: PRT
<213> ORGANISM: Homo Sapiens

<400> SEQUENCE: 16

Met Thr Pro Ala Leu Thr Ala Leu Leu Cys Leu Gly Leu Ser Leu Gly
  1               5                  10                  15

Pro Arg Thr Arg Val Gln Ala Gly Pro Phe Pro Lys Pro Thr Leu Trp
                20                  25                  30

Ala Glu Pro Gly Ser Val Ile Ser Trp Gly Ser Pro Val Thr Ile Trp
            35                  40                  45

Cys Gln Gly Ser Gln Glu Ala Gln Glu Tyr Arg Leu His Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Met Val Met Thr Gly Ala Tyr Ser Lys Pro Thr Leu Ser Ala
    115                 120                 125

Leu Pro Ser Pro Val Val Ala Ser Gly Gly Asn Met Thr Leu Arg Cys
130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Arg Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Thr Asn Thr Pro Trp Val Trp Ser
    195                 200                 205

His Pro Ser Asp Pro Leu Glu Ile Leu Pro Ser Gly Val Ser Arg Lys
210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asn Arg Phe Val Leu
                245                 250                 255
```

```
Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser Asn Gly Gly Gln Tyr Arg Cys Tyr Gly Ala His Asn Leu Ser Ser
290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
        340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser His Pro Ser Glu Pro Leu Glu Leu
                405                 410                 415

Val Val Ser Gly His Ser Gly Gly Ser Ser Leu Pro Pro Thr Gly Pro
        420                 425                 430

Pro Ser Thr Pro Gly Leu Gly Arg Tyr Leu Glu Val Leu Ile Gly Val
        435                 440                 445

Ser Val Ala Phe Val Leu Leu Phe Leu Leu Leu Phe Leu Leu Leu
450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
        500                 505                 510

Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
                565                 570                 575

Asp Arg Gln Met Asp Thr Glu Ala Ala Ala Ser Glu Ala Ser Gln Asp
        580                 585                 590

Val Thr Tyr Ala Gln Leu His Ser Leu Thr Leu Arg Arg Lys Ala Thr
        595                 600                 605

Glu Pro Pro Pro Ser Gln Glu Gly Glu Pro Pro Ala Glu Pro Ser Ile
610                 615                 620

Tyr Ala Thr Leu Ala Ile His
625                 630

<210> SEQ ID NO 17
<211> LENGTH: 591
<212> TYPE: PRT
<213> ORGANISM: Homo Sapiens

<400> SEQUENCE: 17
```

```
Met Thr Leu Thr Leu Ser Val Leu Ile Cys Leu Gly Leu Ser Val Gly
 1               5                  10                 15

Pro Arg Thr Cys Val Gln Ala Gly Thr Leu Pro Lys Pro Thr Leu Trp
             20                  25                 30

Ala Glu Pro Ala Ser Val Ile Ala Arg Gly Lys Pro Val Thr Leu Trp
             35                  40                 45

Cys Gln Gly Pro Leu Glu Thr Glu Tyr Arg Leu Asp Lys Glu Gly
     50                  55                  60

Leu Pro Trp Ala Arg Lys Arg Gln Asn Pro Leu Glu Pro Gly Ala Lys
 65             70                  75                 80

Ala Lys Phe His Ile Pro Ser Thr Val Tyr Asp Ser Ala Gly Arg Tyr
                 85                  90                 95

Arg Cys Tyr Tyr Glu Thr Pro Ala Gly Trp Ser Glu Pro Ser Asp Pro
             100                 105                110

Leu Glu Leu Val Ala Thr Gly Phe Tyr Ala Glu Pro Thr Leu Leu Ala
             115                 120                 125

Leu Pro Ser Pro Val Val Ala Ser Gly Gly Asn Val Thr Leu Gln Cys
 130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
             165                 170                 175

Gln Ala Leu Phe Pro Val Gly Pro Val Thr Pro Ser Cys Arg Trp Arg
             180                 185                 190

Phe Arg Cys Tyr Tyr Tyr Arg Lys Asn Pro Gln Val Trp Ser Asn
             195                 200                 205

Pro Ser Asp Leu Leu Glu Ile Leu Val Pro Gly Val Ser Arg Lys Pro
210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
             245                 250                 255

Lys Glu Gly Glu His Asp Leu Val Gln Gly Ser Gly Gln Gln Pro Gln
             260                 265                 270

Ala Gly Leu Ser Gln Ala Asn Phe Thr Leu Gly Pro Val Ser Arg Ser
             275                 280                 285

His Gly Gly Gln Tyr Arg Cys Tyr Gly Ala His Asn Leu Ser Pro Arg
             290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
             325                 330                 335

Gly Glu Asn Val Thr Leu Leu Cys Gln Ser Trp His Gln Ile Asp Thr
             340                 345                 350

Phe Phe Leu Thr Lys Glu Gly Ala Ala His Pro Pro Leu Cys Leu Lys
             355                 360                 365

Ser Lys Tyr Gln Ser Tyr Arg His Gln Ala Glu Phe Ser Met Ser Pro
             370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
             405                 410                 415

Val Ser Gly Pro Ser Gly Asp Pro Ser Leu Ser Pro Thr Gly Ser Thr
             420                 425                 430
```

-continued

```
Pro Thr Pro Ala Gly Pro Glu Asp Gln Pro Leu Thr Pro Thr Gly Leu
        435                 440                 445

Asp Pro Gln Ser Gly Leu Gly Arg His Leu Gly Val Val Thr Gly Val
        450                 455                 460

Ser Val Ala Phe Val Leu Leu Leu Phe Leu Leu Leu Phe Leu Leu Leu
465                 470                 475                 480

Arg His Arg His Gln Ser Lys His Arg Thr Ser Ala His Phe Tyr Arg
                    485                 490                 495

Pro Ala Gly Ala Ala Gly Pro Glu Pro Lys Asp Gln Gly Leu Gln Lys
                500                 505                 510

Arg Ala Ser Pro Val Ala Asp Ile Gln Glu Glu Ile Leu Asn Ala Ala
        515                 520                 525

Val Lys Asp Thr Gln Pro Lys Asp Gly Val Glu Met Asp Ala Arg Ala
        530                 535                 540

Ala Ala Ser Glu Ala Pro Gln Asp Val Thr Tyr Ala Gln Leu His Ser
545                 550                 555                 560

Leu Thr Leu Arg Arg Glu Ala Thr Glu Pro Pro Ser Gln Glu Arg
                    565                 570                 575

Glu Pro Pro Ala Glu Pro Ser Ile Tyr Ala Pro Leu Ala Ile His
                580                 585                 590
```

```
<210> SEQ ID NO 18
<211> LENGTH: 590
<212> TYPE: PRT
<213> ORGANISM: Homo Sapiens

<400> SEQUENCE: 18
```

```
Met Thr Leu Thr Leu Ser Val Leu Ile Cys Leu Gly Leu Ser Val Gly
 1               5                  10                  15

Pro Arg Thr Cys Val Gln Ala Gly Thr Leu Pro Lys Pro Thr Leu Trp
                20                  25                  30

Ala Glu Pro Ala Ser Val Ile Ala Arg Gly Lys Pro Val Thr Leu Trp
            35                  40                  45

Cys Gln Gly Pro Leu Glu Thr Glu Glu Tyr Arg Leu Asp Lys Glu Gly
        50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                    85                  90                  95

Arg Cys Tyr Tyr Glu Thr Pro Ala Gly Trp Ser Glu Pro Ser Asp Pro
                100                 105                 110

Leu Glu Leu Val Ala Thr Gly Phe Tyr Ala Glu Pro Thr Leu Leu Ala
            115                 120                 125

Leu Pro Ser Pro Val Val Ala Ser Gly Gly Asn Val Thr Leu Gln Cys
        130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                    165                 170                 175

Gln Ala Leu Phe Pro Val Gly Pro Val Thr Pro Ser Cys Arg Trp Arg
                180                 185                 190

Phe Arg Cys Tyr Tyr Tyr Tyr Arg Lys Asn Pro Gln Val Trp Ser Asn
            195                 200                 205

Pro Ser Asp Leu Leu Glu Ile Leu Val Pro Gly Val Ser Arg Lys Pro
        210                 215                 220
```

```
Ser Leu Leu Ile Pro Gln Gly Ser Val Ala Arg Gly Ser Leu
225                 230                 235                 240

Thr Leu Gln Cys Arg Ser Asp Val Gly Tyr Asp Ile Phe Val Leu Tyr
            245                 250                 255

Lys Glu Gly Glu His Asp Leu Val Gln Gly Ser Gly Gln Pro Gln
        260                 265                 270

Ala Gly Leu Ser Gln Ala Asn Phe Thr Leu Gly Pro Val Ser Arg Ser
        275                 280                 285

His Gly Gly Gln Tyr Arg Cys Tyr Gly Ala His Asn Leu Ser Pro Arg
        290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
                340                 345                 350

Phe Phe Leu Thr Lys Glu Gly Ala Ala His Pro Pro Leu Cys Leu Lys
            355                 360                 365

Ser Lys Tyr Gln Ser Tyr Arg His Gln Ala Glu Phe Ser Met Ser Pro
        370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415

Val Ser Gly Pro Ser Gly Asp Pro Ser Leu Ser Pro Thr Gly Ser Thr
                420                 425                 430

Pro Thr Pro Gly Pro Glu Asp Gln Pro Leu Thr Pro Thr Gly Leu Asp
            435                 440                 445

Pro Gln Ser Gly Leu Gly Arg His Leu Gly Val Val Thr Gly Val Ser
            450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                485                 490                 495

Ala Gly Ala Ala Gly Pro Glu Pro Lys Asp Gln Gly Leu Gln Lys Arg
                500                 505                 510

Ala Ser Pro Val Ala Asp Ile Gln Glu Glu Ile Leu Asn Ala Ala Val
            515                 520                 525

Lys Asp Thr Gln Pro Lys Asp Gly Val Glu Met Asp Ala Arg Ala Ala
        530                 535                 540

Ala Ser Glu Ala Pro Gln Asp Val Thr Tyr Ala Gln Leu His Ser Leu
545                 550                 555                 560

Thr Leu Arg Arg Glu Ala Thr Glu Pro Pro Pro Ser Gln Glu Arg Glu
                565                 570                 575

Pro Pro Ala Glu Pro Ser Ile Tyr Ala Pro Leu Ala Ile His
                580                 585                 590

<210> SEQ ID NO 19
<211> LENGTH: 491
<212> TYPE: PRT
<213> ORGANISM: Homo Sapiens

<400> SEQUENCE: 19

Met Thr Leu Thr Leu Ser Val Leu Ile Cys Leu Gly Leu Ser Val Gly
1               5                   10                  15
```

```
Pro Arg Thr Cys Val Gln Ala Gly Thr Leu Pro Lys Pro Thr Leu Trp
                20                  25                  30

Ala Glu Pro Ala Ser Val Ile Ala Arg Gly Lys Pro Val Thr Leu Trp
                35                  40                  45

Cys Gln Gly Pro Leu Glu Thr Glu Glu Tyr Arg Leu Asp Lys Glu Gly
 50                          55                  60

Leu Pro Trp Ala Arg Lys Arg Gln Asn Pro Leu Glu Pro Gly Ala Lys
 65                  70                  75                  80

Ala Lys Phe His Ile Pro Ser Thr Val Tyr Asp Ser Ala Gly Arg Tyr
                 85                  90                  95

Arg Cys Tyr Tyr Glu Thr Pro Ala Gly Trp Ser Glu Pro Ser Asp Pro
                100                 105                 110

Leu Glu Leu Val Ala Thr Gly Val Ser Arg Lys Pro Ser Leu Leu Ile
                115                 120                 125

Pro Gln Gly Ser Val Val Ala Arg Gly Gly Ser Leu Thr Leu Gln Cys
130                 135                 140

Arg Ser Asp Val Gly Tyr Asp Ile Phe Val Leu Tyr Lys Glu Gly Glu
145                 150                 155                 160

His Asp Leu Val Gln Gly Ser Gly Gln Gln Pro Gln Ala Gly Leu Ser
                165                 170                 175

Gln Ala Asn Phe Thr Leu Gly Pro Val Ser Arg Ser His Gly Gly Gln
                180                 185                 190

Tyr Arg Cys Tyr Gly Ala His Asn Leu Ser Pro Arg Trp Ser Ala Pro
                195                 200                 205

Ser Asp Pro Leu Asp Ile Leu Ile Ala Gly Leu Ile Pro Asp Ile Pro
210                 215                 220

Ala Leu Ser Val Gln Pro Gly Pro Lys Val Ala Ser Gly Glu Asn Val
225                 230                 235                 240

Thr Leu Leu Cys Gln Ser Trp His Gln Ile Asp Thr Phe Phe Leu Thr
                245                 250                 255

Lys Glu Gly Ala Ala His Pro Pro Leu Cys Leu Lys Ser Lys Tyr Gln
                260                 265                 270

Ser Tyr Arg His Gln Ala Glu Phe Ser Met Ser Pro Val Thr Ser Ala
                275                 280                 285

Gln Gly Gly Thr Tyr Arg Cys Tyr Ser Ala Ile Arg Ser Tyr Pro Tyr
                290                 295                 300

Leu Leu Ser Ser Pro Ser Tyr Pro Gln Glu Leu Val Val Ser Gly Pro
305                 310                 315                 320

Ser Gly Asp Pro Ser Leu Ser Pro Thr Gly Ser Thr Pro Thr Pro Ala
                325                 330                 335

Gly Pro Glu Asp Gln Pro Leu Thr Pro Thr Gly Leu Asp Pro Gln Ser
                340                 345                 350

Gly Leu Gly Arg His Leu Gly Val Val Thr Gly Val Ser Val Ala Phe
                355                 360                 365

Val Leu Leu Leu Phe Leu Leu Phe Leu Leu Leu Arg His Arg His
                370                 375                 380

Gln Ser Lys His Arg Thr Ser Ala His Phe Tyr Arg Pro Ala Gly Ala
385                 390                 395                 400

Ala Gly Pro Glu Pro Lys Asp Gln Gly Leu Gln Lys Arg Ala Ser Pro
                405                 410                 415

Val Ala Asp Ile Gln Glu Glu Ile Leu Asn Ala Ala Val Lys Asp Thr
                420                 425                 430

Gln Pro Lys Asp Gly Val Glu Met Asp Ala Arg Ala Ala Ala Ser Glu
```

```
                    435                 440                 445
Ala Pro Gln Asp Val Thr Tyr Ala Gln Leu His Ser Leu Thr Leu Arg
    450                 455                 460

Arg Glu Ala Thr Glu Pro Pro Ser Gln Glu Arg Glu Pro Pro Ala
465                 470                 475                 480

Glu Pro Ser Ile Tyr Ala Pro Leu Ala Ile His
                485                 490

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
tgaaggctct cattggagtg tctg                                          24
```